(12) United States Patent
Kimball et al.

(10) Patent No.: US 11,456,068 B2
(45) Date of Patent: *Sep. 27, 2022

(54) SURGICAL INSTRUMENT USAGE DATA MANAGEMENT

(71) Applicant: Cilag GmbH International, Zug (CH)

(72) Inventors: Cory G. Kimball, Hamilton, OH (US); Daniel W. Price, Cincinnati, OH (US); William E. Clem, Bozeman, MT (US); Amy L. Marcotte, Mason, OH (US); Danius P. Silkaitis, Seattle, WA (US); John B. Schulte, West Chester, OH (US); Michael R. Lamping, Cincinnati, OH (US); Stephen L. Balek, Springboro, OH (US)

(73) Assignee: Cilag GmbH International, Zug (CH)

( * ) Notice: Subject to any disclaimer, the term of this patent is extended or adjusted under 35 U.S.C. 154(b) by 174 days.

This patent is subject to a terminal disclaimer.

(21) Appl. No.: 16/541,408

(22) Filed: Aug. 15, 2019

(65) Prior Publication Data

US 2020/0045132 A1    Feb. 6, 2020

Related U.S. Application Data

(60) Continuation of application No. 14/832,497, filed on Aug. 21, 2015, now Pat. No. 10,455,052, which is a (Continued)

(51) Int. Cl.
*G06Q 20/08* (2012.01)
*G06F 19/00* (2018.01)
(Continued)

(52) U.S. Cl.
CPC ............. *G16H 20/40* (2018.01); *A61B 17/28* (2013.01); *A61B 17/320092* (2013.01);
(Continued)

(58) Field of Classification Search
CPC ......... H04L 67/32; A61B 90/90; A61B 90/98; A61B 2090/0803; A61B 2090/0804;
(Continued)

(56) References Cited

U.S. PATENT DOCUMENTS 5,980,510 A    11/1999 Tsonton et al.
6,471,637 B1   10/2002 Chatenever et al.
(Continued)

FOREIGN PATENT DOCUMENTS

CN    1554061 A    12/2004
CN    101729354 A    6/2010
(Continued)

OTHER PUBLICATIONS

European Summons to Attend Oral Proceedings dated Feb. 20, 2020 for Application No. 13160476.1, 9 pages.
(Continued)

*Primary Examiner* — Boniface Ngathi N
(74) *Attorney, Agent, or Firm* — Frost Brown Todd LLC

(57) ABSTRACT

A surgical instrument operable to sever tissue includes a body assembly and a selectively coupleable end effector assembly. The end effector assembly may include a transmission assembly and an end effector. The body assembly includes a trigger and a casing configured to couple with the transmission assembly. An information transmission system transmits instrument information received from a sensor, for example, to a secure server via a secure gateway connected to the instrument. The instrument may be previously tested on a calibration kit to pre-determine and load surgeon-specific settings onto the instrument prior to use.

20 Claims, 16 Drawing Sheets

Related U.S. Application Data division of application No. 13/426,792, filed on Mar. 22, 2012, now abandoned.

(51) Int. Cl.

| | | |
|---|---|---|
| *A61B 17/28* | (2006.01) | |
| *A61B 17/32* | (2006.01) | |
| *A61B 18/14* | (2006.01) | |
| *G16H 20/40* | (2018.01) | |
| *H04L 67/60* | (2022.01) | |
| *A61B 90/90* | (2016.01) | |
| *A61B 90/98* | (2016.01) | |
| *G16H 40/63* | (2018.01) | |
| *A61B 17/00* | (2006.01) | |
| *A61B 17/29* | (2006.01) | |
| *A61B 18/00* | (2006.01) | |
| *A61B 90/00* | (2016.01) | |

(52) U.S. Cl.
CPC .......... *A61B 18/1445* (2013.01); *A61B 90/90* (2016.02); *A61B 90/98* (2016.02); *G06Q 20/085* (2013.01); *G16H 40/63* (2018.01); *H04L 67/32* (2013.01); *A61B 2017/00017* (2013.01); *A61B 2017/00026* (2013.01); *A61B 2017/0046* (2013.01); *A61B 2017/00221* (2013.01); *A61B 2017/00464* (2013.01); *A61B 2017/00477* (2013.01); *A61B 2017/00725* (2013.01); *A61B 2017/2931* (2013.01); *A61B 2017/320093* (2017.08); *A61B 2017/320094* (2017.08); *A61B 2017/320095* (2017.08); *A61B 2017/320097* (2017.08); *A61B 2018/0063* (2013.01); *A61B 2018/00988* (2013.01); *A61B 2090/0803* (2016.02); *A61B 2090/0804* (2016.02); *A61B 2090/0807* (2016.02)

(58) Field of Classification Search
CPC ............ A61B 2090/0807; A61B 17/28; A61B 17/320092; A61B 2017/00725; A61B 2017/00464; A61B 2017/0046; A61B 2017/00026; A61B 2017/00017; A61B 2017/2931; A61B 2017/00221; A61B 18/1445; A61B 2018/0063; A61B 2018/00988; G06Q 20/085
See application file for complete search history.

(56) References Cited

U.S. PATENT DOCUMENTS

| | | |
|---|---|---|
| 6,500,176 B1 | 12/2002 | Truckai et al. |
| 6,666,860 B1 | 12/2003 | Takahashi |
| 6,740,085 B2 | 5/2004 | Hareyama et al. |
| 6,761,698 B2 | 7/2004 | Shibata et al. |
| 6,783,524 B2 | 8/2004 | Anderson et al. |
| 7,082,460 B2 | 7/2006 | Hansen et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,198,630 B2 | 4/2007 | Lipow |
| 7,220,951 B2 | 5/2007 | Truckai et al. |
| 7,244,257 B2 | 7/2007 | Podhajsky et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,416,101 B2 | 8/2008 | Shelton, IV et al. |
| 7,422,582 B2 | 9/2008 | Malackowski et al. |
| 7,546,385 B1 | 6/2009 | Henry et al. |
| 7,594,916 B2 | 9/2009 | Weinberg |
| 7,638,958 B2 | 12/2009 | Philipp et al. |
| 7,695,485 B2 | 4/2010 | Whitman et al. |
| 7,738,971 B2 | 6/2010 | Swayze et al. |
| 7,955,327 B2 | 6/2011 | Sartor et al. |
| 8,147,485 B2 | 4/2012 | Wham et al. |
| 8,181,246 B2 | 5/2012 | Shulman et al. |
| 8,216,223 B2 | 7/2012 | Wham et al. |
| 8,246,608 B2 | 8/2012 | Omori et al. |
| 8,419,757 B2 | 4/2013 | Smith et al. |
| 8,461,744 B2 | 6/2013 | Wiener et al. |
| 8,464,318 B1 | 6/2013 | Hallak |
| 8,566,115 B2 | 10/2013 | Moore |
| 8,657,174 B2 | 2/2014 | Yates et al. |
| 8,852,118 B2 | 10/2014 | Woodruff et al. |
| 8,882,766 B2 | 11/2014 | Couture et al. |
| 8,939,974 B2 | 1/2015 | Boudreaux et al. |
| 8,986,302 B2 | 3/2015 | Aldridge et al. |
| 8,998,797 B2 | 4/2015 | Omori |
| 8,998,939 B2 | 4/2015 | Price et al. |
| 9,023,071 B2 | 5/2015 | Miller et al. |
| 9,050,125 B2 | 6/2015 | Boudreaux et al. |
| 9,095,346 B2 | 8/2015 | Houser et al. |
| 9,161,803 B2 | 10/2015 | Yates et al. |
| 10,455,052 B2 | 10/2019 | Kimball et al. |
| 2001/0039419 A1 | 11/2001 | Francischelli et al. |
| 2004/0133189 A1 | 7/2004 | Sakurai |
| 2006/0079874 A1 | 4/2006 | Faller et al. |
| 2007/0191713 A1 | 8/2007 | Eichmann et al. |
| 2007/0197895 A1 | 8/2007 | Nycz et al. |
| 2007/0282333 A1 | 12/2007 | Fortson et al. |
| 2008/0200940 A1 | 8/2008 | Eichmann et al. |
| 2008/0281301 A1 | 11/2008 | DeBoer et al. |
| 2009/0099876 A1 | 4/2009 | Whitman |
| 2009/0222065 A1 | 9/2009 | Dlugos, Jr. et al. |
| 2010/0036405 A1 | 2/2010 | Giordano et al. |
| 2010/0114095 A1 | 5/2010 | Janssen et al. |
| 2010/0161345 A1 | 6/2010 | Cain et al. |
| 2010/0262436 A1 | 10/2010 | Chen et al. |
| 2011/0125138 A1 | 5/2011 | Malinouskas et al. |
| 2011/0238055 A1 | 9/2011 | Kim et al. |
| 2012/0016659 A1 | 1/2012 | Miura et al. |
| 2012/0078243 A1 | 3/2012 | Worrell et al. |
| 2012/0078247 A1 | 3/2012 | Worrell et al. |
| 2012/0116364 A1 | 5/2012 | Houser et al. |
| 2012/0116388 A1 | 5/2012 | Houser et al. |
| 2012/0210223 A1 | 8/2012 | Eppolito |
| 2013/0253480 A1 | 9/2013 | Kimball et al. |

FOREIGN PATENT DOCUMENTS

| | | |
|---|---|---|
| CN | 101816200 A | 8/2010 |
| EP | 1679034 A1 | 7/2006 |
| EP | 1854420 A1 | 11/2007 |
| EP | 1497951 B1 | 11/2009 |
| JP | 2000-514228 A | 10/2000 |
| JP | 2001-243344 A | 9/2001 |
| JP | 2003-263495 A | 9/2003 |
| JP | 2004-280455 A | 10/2004 |
| JP | 2008-259815 A | 10/2008 |
| JP | 2010-075695 A | 4/2010 |
| JP | 2011-104379 A | 6/2011 |
| JP | 2011-218164 A | 11/2011 |
| WO | WO 1994/027516 | 12/1994 |
| WO | WO 2008/131362 A2 | 10/2008 |

OTHER PUBLICATIONS

Australian Office Action, Patent Examination Report No. 1, dated Nov. 16, 2016 for Application No. AU 2013201085, 5 pgs.
Canadian Office Action dated Mar. 14, 2019 for Application No. CA 2,809,441, 4 pgs.
Chinese Search Report dated Jan. 15, 2016 for Application No. CN 201310093970.6, 3 pgs.
Chinese Office Action, Notification of the First Office Action, dated Feb. 2, 2016 for Application No. CN 201310093970.6, 8 pgs.
Chinese Office Action, The Second Office Action, dated Sep. 27, 2016 for Application No. CN 201310093970.6, 5 pgs.

(56) References Cited

OTHER PUBLICATIONS

European Search Report, Partial, dated Jun. 23, 2016 for Application No. EP 13160476.1, 7 pgs.
European Search Report, Extended, and Written Opinion dated Sep. 28, 2016 for Application No. EP 13160476.1, 12 pgs.
European Examination Report dated Jun. 12, 2019 for Application No. EP 13160476.1, 10 pgs.
Japanese Office Action, Notification of Reasons for Refusal, dated Feb. 28, 2017 for Application No. JP 2013-057932, 6 pgs.
U.S. Appl. No. 61/410,603, filed Nov. 5, 2010.
U.S. Appl. No. 13/426,972.
Canadian Office Action dated Nov. 19, 2020 for Application No. CA 2809441, 3 pgs.
European Summons to attend oral proceedings dated Feb. 20, 2020 for Application No. EP 13160476.1, 9 pgs.
European Result of consultation dated Jul. 2, 2020 for Application No. EP 13160476.1. 3 pgs.
European Decision to Grant dated Sep. 9, 2021 for Application EP 13160476.1, 2 pgs.
U.S. Pat. Pub. No. 2013/0253480.
Extended European Search Report dated May 13, 2022, for Application No. 21201014.4, 16 pages.

SURGICAL INSTRUMENT USAGE DATA MANAGEMENT

PRIORITY

This application is a continuation of U.S. patent application Ser. No. 14/832,497, entitled "Surgical Instrument Usage Data Management," filed Aug. 21, 2015, issued as U.S. Pat. No. 10,455,052 on Oct. 22, 2019, which itself is a division of U.S. patent application Ser. No. 13/426,792, entitled "Surgical Instrument Usage Data Management," filed Mar. 22, 2012, published as U.S. Pub. No. 2013/0253480 on Sep. 26, 2013, now abandoned.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Additional examples endoscopic surgical instruments include are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. patent application Ser. No. 13/151,481, entitled "Motor Driven Electrosurgical Device with Mechanical and Electrical Feedback," filed Jun. 2, 2011, issued as U.S. Pat. No. 9,161,803 on Oct. 20, 2015, the disclosure of which is incorporated by reference herein; U.S. patent application Ser. No. 13/269,870, entitled "Surgical Instrument with Modular Shaft and End Effector," filed Oct. 10, 2011, issued as U.S. Pat. No. 9,510,895 on Dec. 6, 2016, the disclosure of which is incorporated by reference herein; U.S. patent application Ser. No. 13/235,660, entitled "Articulation Joint Features for Articulating Surgical Device," filed Sep. 19, 2011, issued as U.S. Pat. No. 9,402,682 on Aug. 2, 2016, the disclosure of which is incorporated by reference herein; U.S. patent application Ser. No. 13/274,805, entitled "Surgical Instrument with Modular End Effector," filed Oct. 17, 2011, issued as U.S. Pat. No. 8,998,939 on Apr. 7, 2015, the disclosure of which is incorporated by reference herein; U.S. patent application Ser. No. 13/276,725, entitled "Medical Device Usage Data Processing," filed Oct. 19, 2011, issued as U.S. Pat. No. 9,095,346 on Aug. 4, 2015, the disclosure of which is incorporated by reference herein; and U.S. patent application Ser. No. 13/276,660, entitled "User Feedback Through Handpiece of Surgical Instrument," filed Oct. 19, 2011, issued as U.S. Pat. No. 9,364,279 on Jun. 14, 2016, the disclosure of which is incorporated by reference herein.

In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
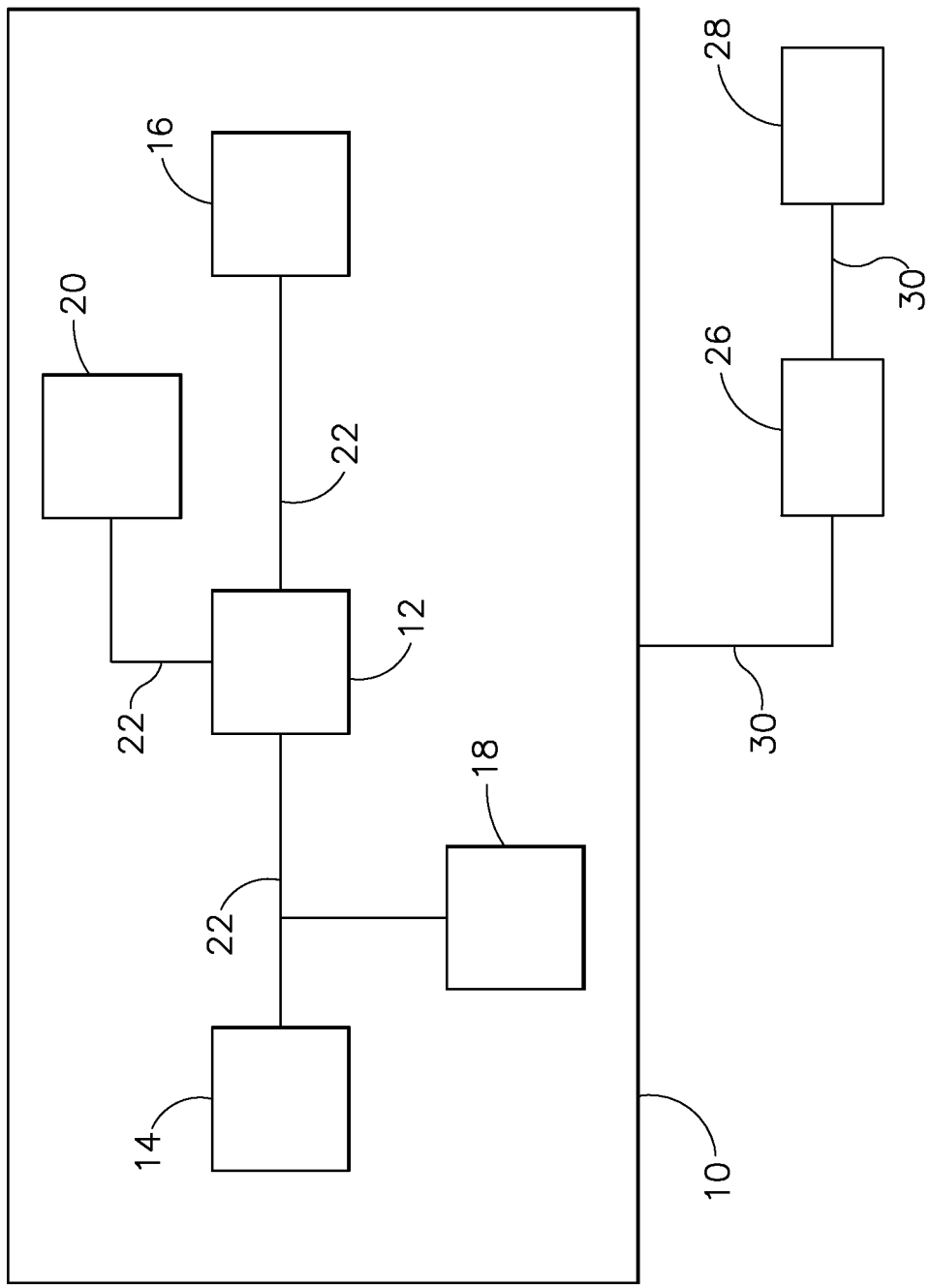
FIG. 1 depicts a schematic view of an exemplary surgical system comprising a medical device having a power source and a cartridge.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should be understood that the teachings below may be readily applied to any of the references that are cited herein. Various suitable ways in which the below teachings may be combined with the references cited herein will be apparent to those of ordinary skill in the art.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Surgical Instrument

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein and as described with respect to FIGS. 3A-3B below. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing impedance in tissue at end effector (16), sensing a temperature at end effector (16), determining movement and/or orientation of end effector (16), or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired. Sensor (20) of medical device (10) may be operable in accordance with the teachings of U.S. patent application Ser. No. 13/276,725, issued as U.S. Pat. No. 9,095,346 on Aug. 4, 2015, the disclosure of which is incorporated by reference herein.

In some versions, a cartridge (26) and generator (28) are attached to medical device (10) via cable (30). For instance, generator (28) may serve as a substitute for power source (14). While medical device (10) is shown as being in communication with both cartridge (26) and generator (28) via cables (30), it should be understood that medical device (10) may alternatively communicate with one or both of cartridge (26) and generator (28) via a wireless communication.

II. Overview of Exemplary Ultrasonic Surgical System

Figure 2:
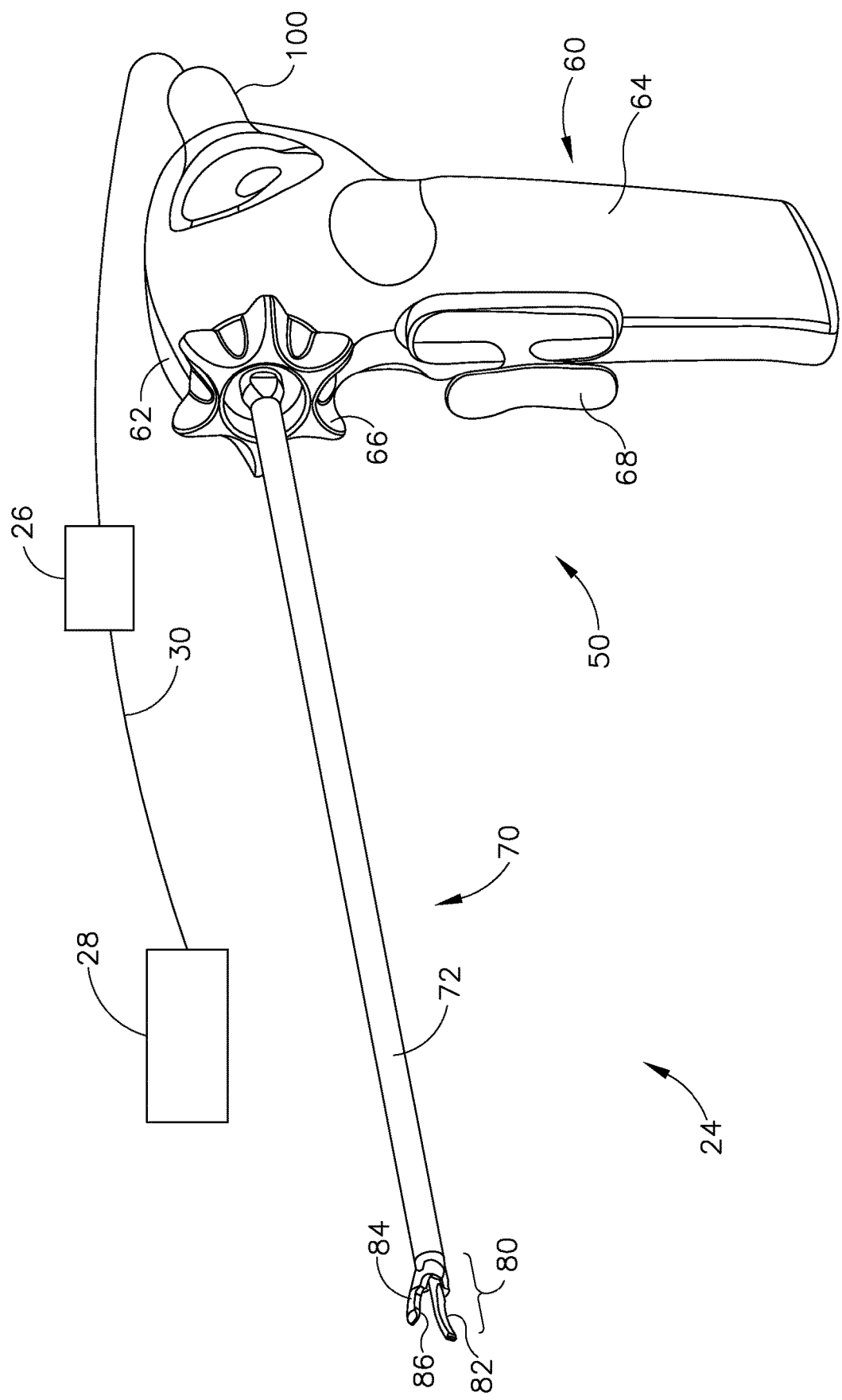
FIG. 2 depicts a perspective view of an exemplary ultrasonic surgical system comprising a surgical instrument and a generator.

FIG. 2 depicts a merely exemplary form that medical device (10) may take. FIG. 2 shows an exemplary ultrasonic surgical system (24) comprising an ultrasonic surgical instrument (50), a cartridge (26), a generator (28), and a cable (30) operable to couple generator (28) to surgical instrument (50). A suitable generator (28) is the GEN 300 sold by Ethicon Endo-Surgery, Inc. of Cincinnati, Ohio. By way of example only, generator (28) may be constructed in accordance with the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, and U.S. patent application Ser. No. 13/269,870, entitled "Surgical Instrument with Modular Shaft and End Effector," filed Oct. 10, 2011, issued as U.S. Pat. No. 9,510,895 on Dec. 6, 2016 the disclosures of which are incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, now abandoned, and U.S. Pat. Pub. No. 2008/0200940, entitled "Ultrasonic Device for Cutting and Coagulating," published Aug. 21, 2008, now abandoned, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). An aperture, described in more detail below, is provided on the distal end of mating housing portion (62) for insertion of various transmission assemblies (70). A rotation knob (66) is shown in the present example to rotate transmission assembly (70) and/or transducer (100), but it should be understood that rotation knob (66) is merely optional. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 the disclosure of which is incorporated by reference herein. Toggle buttons (not shown) may be located on a distal surface of lower portion (64) and may be operable to activate transducer (100) at different operational levels using generator (28). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). The trigger portion may be operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. No. 5,980,510; U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, issued as U.S. Pat. No. 8,939,974 on Jan. 27, 2015; and/or U.S. Pat. Pub. No. 2009/0143797, issued as U.S. Pat. No. 8,419,757 on Apr. 16, 2013. Additional optional configurations and features for surgical instrument (50) are described in U.S. patent application Ser. No. 13/269,899, entitled "Ultrasonic Surgical Instrument with Modular End Effector," filed on Oct. 10, 2011, issued as U.S. Pat. No. 9,050,125 on Jun. 9, 2015, the disclosure of which is incorporated by reference herein.

Figure 3A:
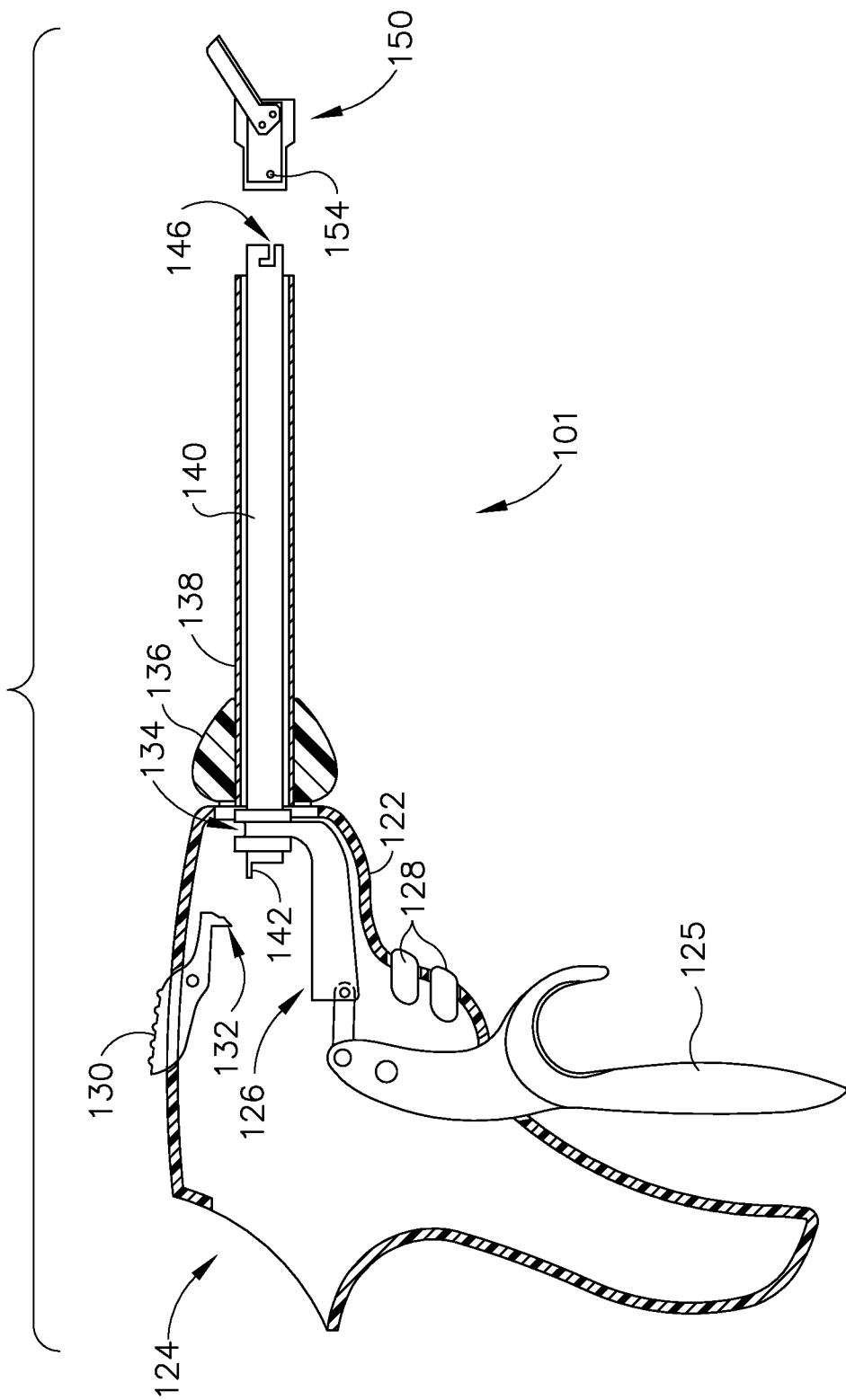
FIG. 3A depicts a cross-sectional side view another exemplary surgical system comprising a surgical instrument with a transducer removed and a detachable end effector.
Figure 3B:
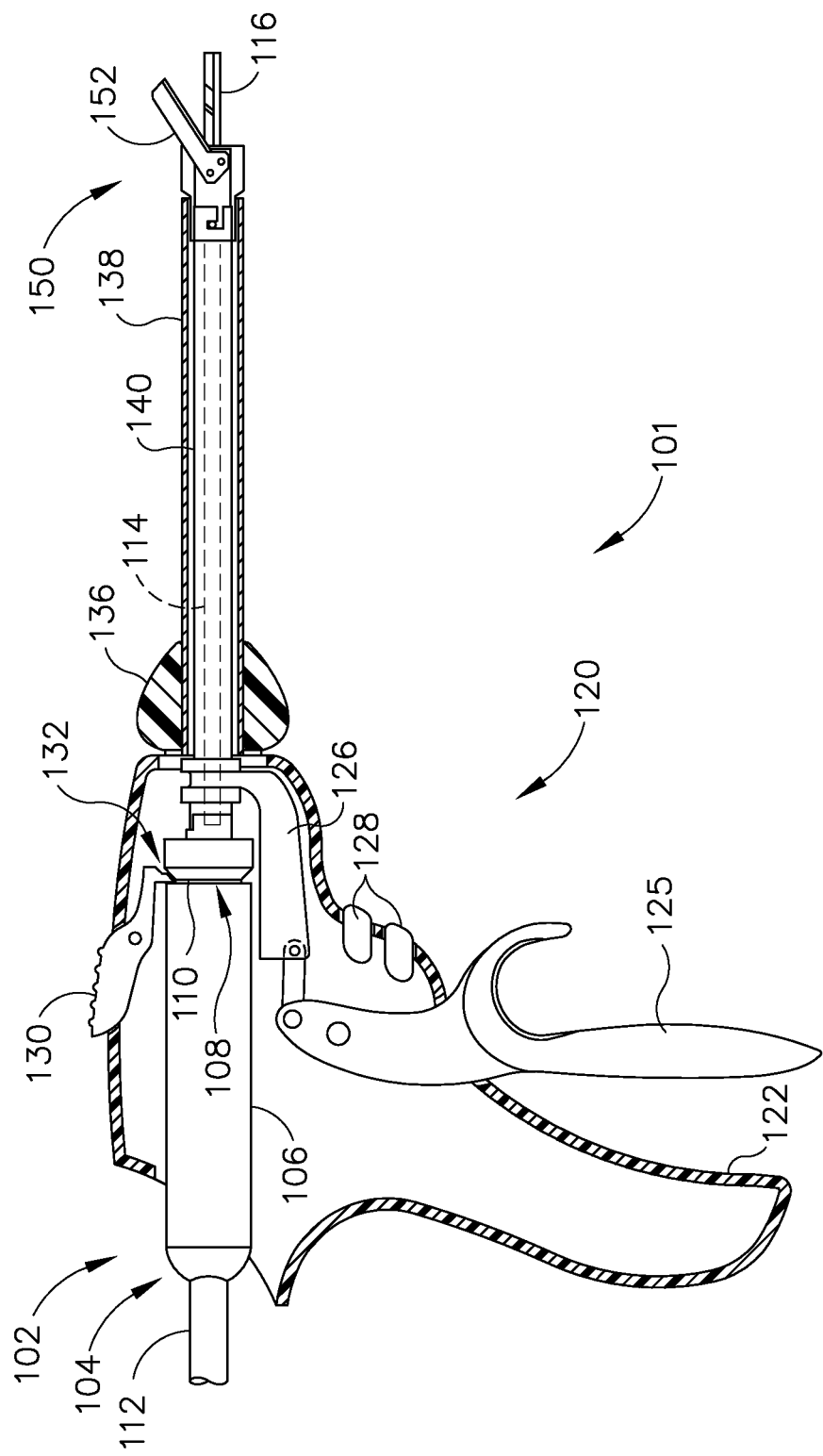
FIG. 3B depicts a cross-sectional side view of the surgical instrument of FIG. 3A with the transducer attached and the detachable end effector attached.

FIGS. 3A-3B depict an alternative version of an ultrasonic instrument (101) having a reusable transducer and blade assembly (102) for use in a handle assembly (120), and a detachable end effector (150). Transducer and blade assembly (102) comprises a transducer (104) and an elongated blade assembly coupled to transducer (104) and extending distally from transducer (104). Traducer (104) is operable to convert electrical power from cable (112) into ultrasonic vibrations at blade (116). Transducer (104) of the present example comprises a transducer body (106), a circumferential notch (108) formed in a distal end of transducer body (106), and a cable (112). Cable (112) of the present example is coupleable to a power source, such as generator (28) described above, to provide power to transducer (104).

It should be understood that transducer (104) may be configured to omit cable (112), such as in a cordless transducer disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013 the disclosure of which is incorporated by reference herein. Components of ultrasonic instrument (101) may be constructed and operable in accordance with the teachings of U.S. patent application Ser. No. 13/274,805, issued as U.S. Pat. No. 8,998,939 on Apr. 7, 2015 which is incorporated by reference herein.

In the present example, casing (122) includes a proximal aperture (124) configured to receive transducer and blade assembly (102). Trigger (125) is pivotably coupled to casing (122) and is configured to pivot from an open position to a closed position. Trigger (125) is configured to actuate outer sheath (138) distally via an actuation assembly (126) when trigger (125) is in the closed position. Toggle buttons (128) comprise buttons operable to selectively activate transducer (104) at different operational levels using a power source and are operable in accordance with the teachings of U.S. patent application Ser. No. 13/274,805, issued as U.S. Pat. No. 8,998,939 on Apr. 7, 2015, which is incorporated by reference herein.

Rotation knob (136) is rotatably coupled to a distal end of casing (122) and is coupled to outer sheath (138) and inner tubular actuation member (140) to rotate outer sheath (138) and inner tubular actuation member (140) relative to casing (122). In some versions, outer sheath (138) and inner tubular actuation member (140) are configured to selectively couple to rotation knob (136).

FIG. 3A shows casing (122) with a proximal aperture (124) configured to receive removable transducer and blade assembly (102). Instrument (101) is capable of accommodating various kinds of transducer and blade assemblies (102), including those with different types of transducer bodies (106) and/or those with different types of blades (116). End effector (150) is shown aligned with outer sheath (138) and inner tubular actuation member (140), but in a detached position. Initially the user inserts transducer and blade assembly (102) through proximal aperture (124). Assembly (102) is guided through inner tubular actuation member (140) and out through the distal end of inner tubular actuation member (140), as shown in FIG. 3B. When transducer and blade assembly (102) is fully inserted, latch member (130) engages notch (108) to retain transducer and blade assembly (102) longitudinally within handle assembly (120). Latch member (130), inner tubular actuation member (140), and transducer and blade assembly (102) may be constructed and operable in accordance with the teachings of U.S. patent application Ser. No. 13/274,805, issued as U.S. Pat. No. 8,998,939 on Apr. 7, 2015, which is incorporated by reference herein. It should be understood that transducer and blade assembly (102) can freely rotate relative to handle assembly (120) while still maintaining an electrical connection between electrical connector (132) and ring connector (110). In addition, as transducer and blade assembly (102) is inserted into handle assembly (120), a user may rotate transducer and blade assembly (102) and/or inner tubular actuation member (140) to align key (142) with a slot (not shown) of assembly (102). Such an alignment maintains the orientation between blade (116) and clamp arm (152) of end effector (150). In some versions, key (142) may be provided on waveguide (114) and/or blade (116) to align inner tubular actuation member (140) with waveguide (114) and/or blade (116). Of course, transducer and blade assembly (102) and/or components thereof may be removably coupled with casing (122) and other components of instrument (101) in numerous other ways as will be apparent to those of ordinary skill in the art in view of the teachings herein.

With transducer and blade assembly (102) axially restrained within handle assembly (120), end effector (150) of the present example is then attached to outer sheath (138) and inner tubular actuation member (140) as shown in FIG. 3B. It should be understood that instrument (101) is capable of accommodating various kinds of end effectors (150) as will be apparent to those of ordinary skill in the art in view of the teachings herein. Outer sheath (138) includes a circumferential groove (134) into which a portion of actuation assembly (126) is insertable. It should be understood that in some versions end effector (150) is coupled to outer sheath (138) and inner tubular actuation member (140) prior to the coupling of transducer and blade assembly (102). In the present example, opposing L-shaped slots (148) of inner tubular actuation member (140) and outer sheath (138) are aligned such that opposing bayonet pins (154) are insertable into longitudinal portions (143) of each L-shaped slot (148). When bayonet pins (154) reach the proximal end of longitudinal portions (143), the user rotates end effector (150) to rotate bayonet pins (154) into radial portions (144) until bayonet pins reach lock portions (146). With end effector (150) and transducer and blade assembly (102) coupled to handle assembly (120), the user may then use the surgical instrument for a procedure. Of course, end effector (150) and/or components thereof may be removably coupled with transducer and blade assembly (102) in numerous other ways as will be apparent to those of ordinary skill in the art in view of the teachings herein.

III. Overview of Exemplary Radiofrequency (RF) Surgical Instrument

Figure 4:
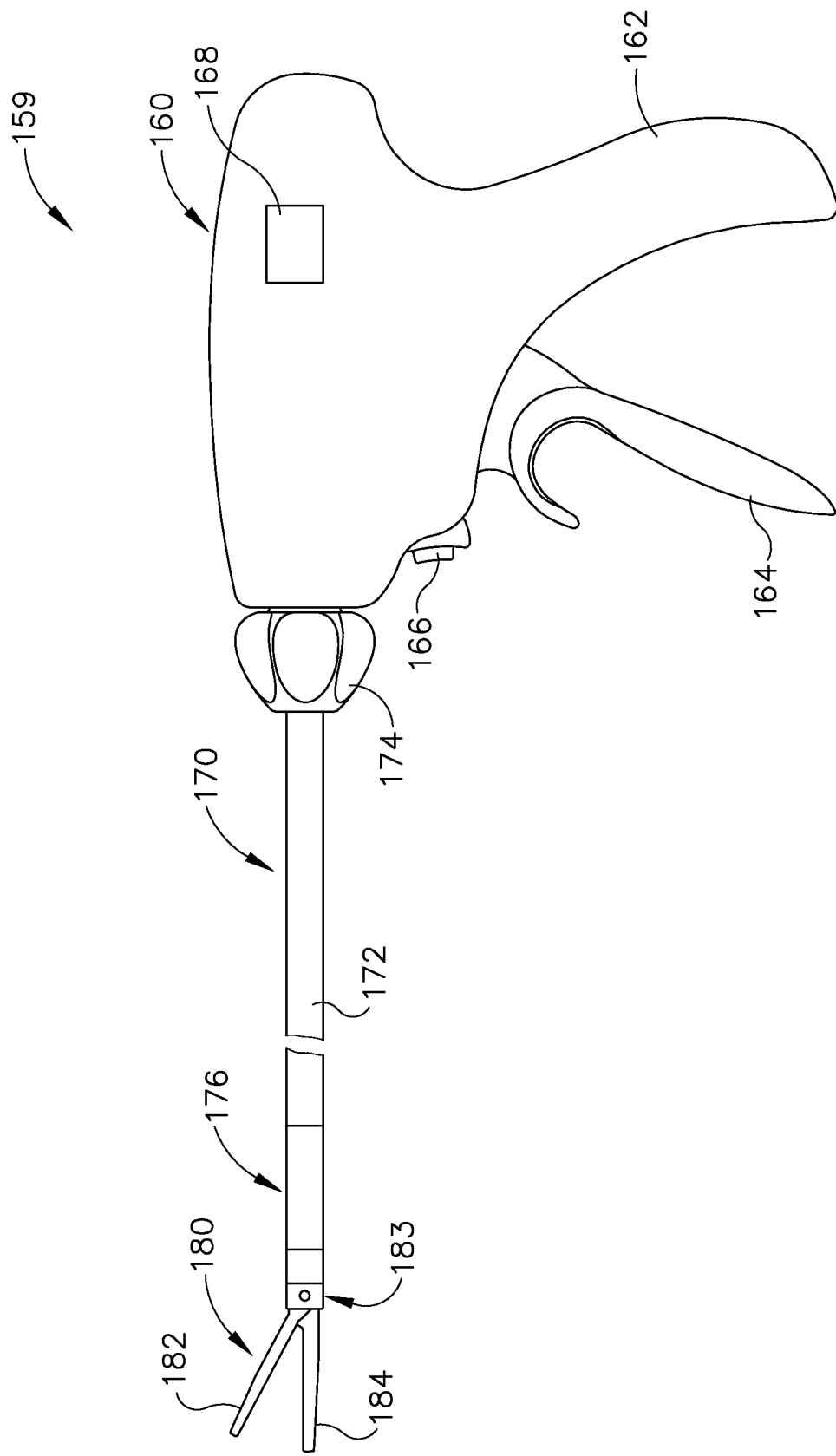
FIG. 4 depicts a side elevation view of an exemplary electrosurgical medical device.

While some surgical instruments are adapted to use ultrasonic energy to operate on tissue, other surgical instruments, such as surgical instrument (159), shown in FIGS. 3-4, can be configured to supply other kinds of energy, such as electrical energy and/or heat energy, to the tissue of a patient.

Figure 5:
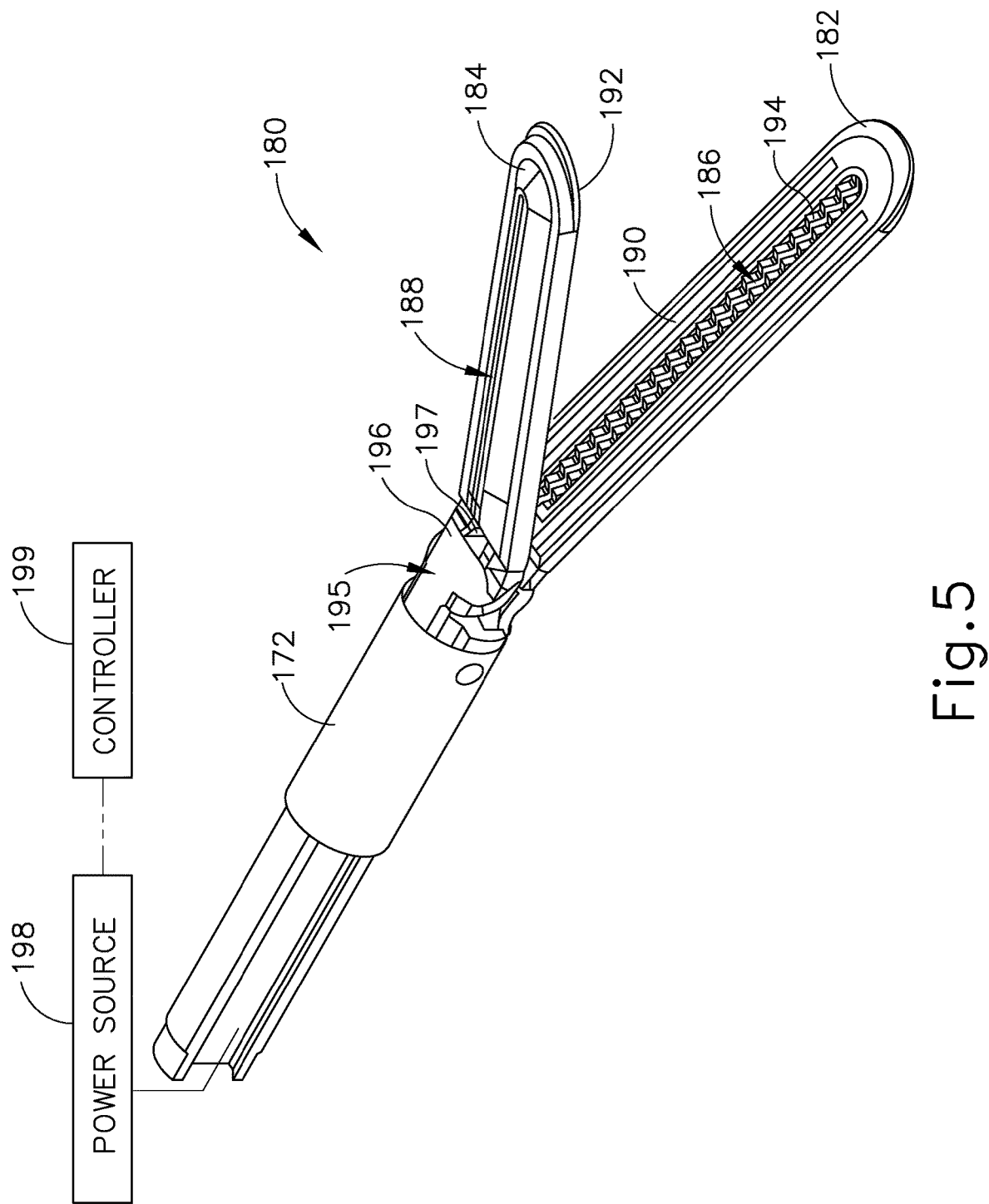
FIG. 5 depicts a perspective view of the end effector of the device of FIG. 4, in an open configuration.

FIGS. 4-5 show an exemplary electrosurgical instrument (159) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, issued as U.S. Pat. No. 8,939, 974 on Jan. 27, 2015; and/or U.S. patent application Ser. No. 13/151,481, issued as U.S. Pat. No. 9,161,803 on Oct. 20, 2015. As described therein and as will be described in greater detail below, electrosurgical instrument (159) is operable to cut tissue and seal or weld tissue (e.g., a blood vessel, etc.) substantially simultaneously. In other words, electrosurgical instrument (159) operates similar to an endocutter type of stapler, except that electrosurgical instrument (159) provides tissue welding through application of bipolar RF energy instead of providing lines of staples to join tissue. It should also be understood that electrosurgical instrument (159) may have various structural and functional similarities with the ENSEAL® Tissue Sealing Device by Ethicon Endo-Surgery, Inc., of Cincinnati, Ohio. Furthermore, electrosurgical instrument (159) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (159), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (159) of the present example includes a handpiece (160), a transmission assembly or shaft (170) extending distally from handpiece (160), and an end effector (180) disposed at a distal end of shaft (170). Handpiece (160) of the present example includes a pistol grip (162), a pivoting trigger (164), an activation button (166), and an articulation control (168). Trigger (164) is pivotable toward and away from pistol grip (162) to selectively actuate end effector (180) as will be described in greater detail below. Activation button (166) is operable to selectively activate RF circuitry that is in communication with end effector (180), in a manner described in U.S. patent application Ser. No. 13/235,660, issued as U.S. Pat. No. 9,402,682 on Aug. 2, 2016, and/or various other references that are cited and incorporated by reference herein. In some versions, activation button (166) also serves as a mechanical lockout against trigger (164), such that trigger (164) cannot be fully actuated unless button (166) is being pressed simultaneously. Examples of how such a lockout may be provided are disclosed in one or more of the references cited herein. It should be understood that pistol grip (162), trigger (164), and button (166) may be modified, substituted, supplemented, etc. in any suitable way, and that the descriptions of such components herein are merely illustrative. Articulation control (168) of the present example is operable to selectively control articulation section (176) of shaft (170) in a manner described in U.S. patent application Ser. No. 13/235,660, issued as U.S. Pat. No. 9,402,682 on Aug. 2, 2016, which is incorporated by reference herein.

Shaft (170) of the present example includes an outer sheath (172) and an articulation section (176). Articulation section (176) is operable to selectively position end effector (180) at various angles relative to the longitudinal axis defined by sheath (172). Various examples of forms that articulation section (176) and other components of shaft (170) may take are described in U.S. patent application Ser. No. 13/235,623, entitled "Control Features for Articulating Surgical Device," filed Sep. 19, 2011, issued as U.S. Pat. No. 9,877,720 on Jan. 30, 2018, the disclosure of which is incorporated by reference herein. For instance, it should be understood that various components that are operable to actuate articulation section (176) may extend through the interior of sheath (172). In some versions, shaft (170) is also rotatable about the longitudinal axis defined by sheath (172), relative to handpiece (160), via a knob (174). Such rotation may provide rotation of end effector (180) and shaft (170) unitarily. In some other versions, knob (174) is operable to rotate end effector (180) without rotating any portion of shaft (170) that is proximal of articulation section (176). As another merely illustrative example, electrosurgical instrument (159) may include one rotation control that provides rotatability of shaft (170) and end effector (180) as a single unit; and another rotation control that provides rotatability of end effector (180) without rotating any portion of shaft (170) that is proximal of articulation section (176). Other suitable rotation schemes will be apparent to those of ordinary skill in the art in view of the teachings herein. Of course, rotatable features may simply be omitted if desired.

B. Exemplary End Effector

End effector (180) of the present example comprises a first jaw (182) and a second jaw (184). In the present example, second jaw (184) is substantially fixed relative to shaft (170); while first jaw (182) pivots relative to shaft (170), toward and away from second jaw (184). In some versions, actuators such as rods or cables, etc., may extend through sheath (172) and be joined with first jaw (182) at a pivotal coupling (183), such that longitudinal movement of the actuator rods/cables/etc. through shaft (170) provides pivoting of first jaw (182) relative to shaft (170) and relative to second jaw (184). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (195), such that actuator rods/cables/etc. may simply be eliminated in some versions.

As best seen in FIGS. 4-5, first jaw (182) defines a longitudinally extending elongate slot (186); while second jaw (184) also defines a longitudinally extending elongate slot (148). In addition, the top side of first jaw (182) presents a first electrode surface (190); while the underside of second jaw (184) presents a second electrode surface (192). Electrode surfaces (190, 192) are in communication with an electrical source (198) via one or more conductors (not shown) that extend along the length of shaft (170). Electrical source (198) is operable to deliver RF energy to first electrode surface (190) at a first polarity and to second electrode surface (192) at a second (opposite) polarity, such that RF current flows between electrode surfaces (190, 192) and thereby through tissue captured between jaws (182, 184). In some versions, firing beam (195) serves as an electrical conductor that cooperates with electrode surfaces (190, 192) (e.g., as a ground return) for delivery of bipolar RF energy captured between jaws (182, 184). Electrical source (198) may be external to electrosurgical instrument (159) or may be integral with electrosurgical instrument (159) (e.g., in handpiece (160), etc.), as described in one or more references cited herein or otherwise. A controller (199) regulates delivery of power from electrical source (198) to electrode surfaces (190, 192). Controller (199) may also be external to electrosurgical instrument (159) or may be integral with electrosurgical instrument (159) (e.g., in handpiece (160), etc.), as described in one or more references cited herein or otherwise. It should also be understood that electrode surfaces (190, 192) may be provided in a variety of alternative locations, configurations, and relationships.

The lower side of first jaw (182) includes a longitudinally extending recess (not shown) adjacent to slot (186); while the upper side of second jaw (184) includes a longitudinally extending recess (not shown) adjacent to slot (188). FIG. 4 shows the upper side of first jaw (182) including a plurality of teeth serrations (194). It should be understood that the lower side of second jaw (184) may include complementary serrations that nest with serrations (194), to enhance gripping of tissue captured between jaws (182, 184) without necessarily tearing the tissue. Serrations (194) may be constructed and operable in accordance with the teachings of U.S. patent application Ser. No. 13/235,660, issued as U.S. Pat. No. 9,402,682 on Aug. 2, 2016, and/or various other references that are cited and incorporated by reference herein.

With jaws (182, 184) in a closed position, shaft (170) and end effector (180) are sized and configured to fit through trocars having various inner diameters, such that electrosurgical instrument (159) is usable in minimally invasive surgery, though of course electrosurgical instrument (159) could also be used in open procedures if desired. Shaft (170) and end effector (180) may be constructed and operable in accordance with the teachings of U.S. patent application Ser.

No. 13/235,660, issued as U.S. Pat. No. 9,402,682 on Aug. 2, 2016, and/or various other references that are cited and incorporated by reference herein.

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (e.g., PTC polymer, etc.), located adjacent to electrodes (190, 192) and/or elsewhere. Data from sensors may be communicated to controller (199). Controller (199) may process such data in a variety of ways. By way of example only, controller (199) may modulate or otherwise change the RF energy being delivered to electrode surfaces (190, 192), based at least in part on data acquired from one or more sensors at end effector (180). In addition or in the alternative, controller (199) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (199), and may simply provide a purely localized effect at end effector (180). For instance, a PTC thermistor bodies (not shown) at end effector (40) may automatically reduce the energy delivery at electrode surfaces (190, 192) as the temperature of the tissue and/or end effector (180) increases, thereby reducing the likelihood of overheating. In some such versions, a PTC thermistor element is in series with power source (198) and electrode surface (190, 192); and the PTC thermistor provides an increased impedance (reducing flow of current) in response to temperatures exceeding a threshold. Furthermore, it should be understood that electrode surfaces (190, 192) may be used as sensors (e.g., to sense tissue impedance, etc.). Various kinds of sensors that may be incorporated into electrosurgical instrument (159) will be apparent to those of ordinary skill in the art in view of the teachings herein. Similarly various things that can be done with data from sensors, by controller (199) or otherwise, will be apparent to those of ordinary skill in the art in view of the teachings herein. Other suitable variations for end effector (180) will also be apparent to those of ordinary skill in the art in view of the teachings herein.

C. Exemplary Firing Beam

As also seen in FIGS. 4-5, electrosurgical instrument (159) of the present example includes a firing beam (195) that is longitudinally movable along part of the length of end effector (180). Firing beam (195) is coaxially positioned within shaft (170), extends along the length of shaft (170), and translates longitudinally within shaft (170) (including articulation section (176) in the present example), though it should be understood that firing beam (195) and shaft (170) may have any other suitable relationship. Firing beam (195) includes a sharp distal blade (197), an upper flange (196), and a lower flange (not shown). Firing beam (195) may be constructed and operable in accordance with the teachings of U.S. patent application Ser. No. 13/235,660, issued as U.S. Pat. No. 9,402,682 on Aug. 2, 2016, and/or various other references that are cited and incorporated by reference herein. Distal blade (197) extends through slots (186, 188) of jaws (182, 184), with upper flange (196) being located above jaw (184) in a recess (not shown) and the lower flange (not shown) being located below jaw (182) in a recess (not shown). The configuration of distal blade (197), upper flange (196), and the lower flange (not shown) provides an "I-beam" type of cross section at the distal end of firing beam (195) and may be constructed and operable in accordance with the teachings of U.S. patent application Ser. No. 13/235,660, issued as U.S. Pat. No. 9,402,682 on Aug. 2, 2016, and/or various other references that are cited and incorporated by reference herein.

Distal blade (197) is substantially sharp, such that distal blade will readily sever tissue that is captured between jaws (182, 184). Distal blade (197) is also electrically grounded in the present example, providing a return path for RF energy as described elsewhere herein. In some other versions, distal blade (197) serves as an active electrode. In addition or in the alternative, distal blade (197) may be selectively energized with ultrasonic energy (e.g., harmonic vibrations at approximately 55.5 kHz, etc.).

The "I-beam" type of configuration of firing beam (195) provides closure of jaws (182, 184) as firing beam (195) is advanced distally. In particular, flange (196) urges jaw (184) pivotally toward jaw (182) as firing beam (195) is advanced from a proximal position to a distal position, by bearing against a recess (not shown) formed in jaw (184). This closing effect on jaws (182, 184) by firing beam (195) may occur before distal blade (197) reaches tissue captured between jaws (182, 184). Such staging of encounters by firing beam (195) may reduce the force required to squeeze grip (164) to actuate firing beam (195) through a full firing stroke. In other words, in some such versions, firing beam (195) may have already overcome an initial resistance required to substantially close jaws (182, 184) on tissue before encountering resistance from the tissue captured between jaws (182, 184). Of course, any other suitable staging may be provided.

In the present example, flange (196) is configured to cam against a ramp feature at the proximal end of jaw (184) to open jaw (182) when firing beam (195) is retracted to a proximal position and to hold jaw (182) open when firing beam (195) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (195) is translated in the present example, it should be understood that other versions may provide independent movement of jaws (182, 184) and firing beam (195). By way of example only, one or more cables, rods, beams, or other features may extend through shaft (170) to selectively actuate jaws (182, 184) independently of firing beam (195). Such jaw (182, 184) actuation features may be separately controlled by a dedicated feature of handpiece (160). Alternatively, such jaw actuation features may be controlled by trigger (164) in addition to having trigger (164) control firing beam (195). It should also be understood that firing beam (195) may be resiliently biased to a proximal position, such that firing beam (195) retracts proximally when a user relaxes their grip on trigger (164).

D. Exemplary Operation

In an exemplary use, end effector (180) is inserted into a patient via a trocar. Articulation section (176) is substantially straight when end effector (180) and part of shaft (170) are inserted through the trocar. Articulation control (168) may then be manipulated to pivot or flex articulation section (176) of shaft (170) in order to position end effector (180) at a desired position and orientation relative to an anatomical structure within the patient. Two layers of tissue of the anatomical structure are then captured between jaws (182, 184) by squeezing trigger (164) toward pistol grip (162). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (159) is perpendicular to the longitudinal axis defined by end effector (180), etc.). In other words, the lengths of jaws (182, 184) may be oriented perpendicular to (or at least generally transverse to) the length of the blood vessel. As noted above, flanges (162, 166) cammingly act to pivot jaw (182) toward jaw (184) when firing beam (195) is actuated distally by squeezing trigger (164) toward pistol grip (162).

With tissue layers captured between jaws (182, 184) firing beam (195) continues to advance distally by the user squeezing trigger (164) toward pistol grip (162). As firing beam (195) advances distally, distal blade (197) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of upper flange (162) and the lower flange (not shown) immediately above and below jaws (182, 184), respectively, may help keep jaws (182, 184) in a closed and tightly clamping position. In particular, flanges (162, 166) may help maintain a significantly compressive force between jaws (182, 184). With severed tissue layer portions being compressed between jaws (182, 184), electrode surfaces (190, 192) are activated with bipolar RF energy by the user depressing activation button (166). In some versions, electrodes (190, 192) are selectively coupled with power source (198) (e.g., by the user depressing button (166), etc.) such that electrode surfaces (190, 192) of jaws (182, 184) are activated with a common first polarity while firing beam (195) is activated at a second polarity that is opposite to the first polarity. Thus, a bipolar RF current flows between firing beam (195) and electrode surfaces (190, 192) of jaws (182, 184), through the compressed regions of severed tissue layer portions. In some other versions, electrode surface (190) has one polarity while electrode surface (192) and firing beam (195) both have the other polarity. In either version (among at least some others), bipolar RF energy delivered by power source (198) ultimately thermally welds the tissue layer portions on one side of firing beam (195) together and the tissue layer portions on the other side of firing beam (195) together.

In certain circumstances, the heat generated by activated electrode surfaces (190, 192) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (190, 192) may be activated with bipolar RF energy before firing beam (195) even begins to translate distally and thus before the tissue is even severed. For instance, such timing may be provided in versions where button (166) serves as a mechanical lockout relative to trigger (164) in addition to serving as a switch between power source (198) and electrode surfaces (190, 192).

While several of the teachings below are described as variations of instruments (10, 50, 101, 159), it should be understood that various teachings below may also be incorporated into various other types of devices. By way of example only, in addition to being readily incorporated into instruments (10, 50, 101, 159), various teachings below may be readily incorporated into the devices taught in any of the references cited herein, surgical staplers, surgical clip appliers, and tissue graspers, among various other devices. Other suitable devices into which the following teachings may be incorporated will be apparent to those of ordinary skill in the art in view of the teachings herein. Of course end effectors (16, 80, 150, 180) and surgical instruments (10, 50, 101, 159) may also include other configurations as will be apparent to one of ordinary skill in the art in view of the teachings herein.

IV. Exemplary Coupling Mechanisms for Modular Shafts and End Effectors

In some instances it may be useful to change between various shaft lengths and/or types of end effectors (16, 80, 150, 180) while using the same handle assembly (60, 120, 160). For instance, in some procedures, a large amount of tissue may need to be cut, requiring different length end effectors (80, 150, 180) and/or shafts for transmission assemblies (70, 102, 170). Such interchangeable shafts and/or end effectors (80, 150, 180) may permit a common handle assembly (60, 120, 160) to be used for various surgical procedures (e.g., short shafts for open surgery, long shafts for minimally invasive laparoscopic surgery, etc.). Moreover, changing out the shafts and/or the end effectors (80, 150, 180) while reusing the same handle assembly (60, 120, 160) may be more time and/or cost effective than using a new surgical instrument (50, 101, 159) with the different length shaft. By way of example only, such shafts and/or end effectors (80, 150, 180) may include color codes to distinguish the various lengths and/or types. In another instance, the handle assembly (60, 120, 160) may be configured to employ different types of end effectors, for instance, the handle assembly (60, 120, 160) may include components to operate an ultrasonic end effector (80, 150) and/or an RF end effector (180). Thus, changing the shafts and end effectors (80, 150, 180) with a common handle assembly (60, 120, 160) may conserve time and/or costs. Accordingly, various coupling mechanisms for coupling the modular shafts to the handle assemblies (60, 120, 160) are described below. It should be understood that in versions where an ultrasonic end effector (80) is used, at least part of transducer (100) may be integral with the shaft and end effector (80), and may thus be selectively coupled with handle assembly (60). Alternatively, transducer (100) may be integral with handle assembly (60) such that the shaft and end effector (80) are selectively coupled with transducer (100) when the shaft and end effector (80) are selectively coupled with handle assembly (60).

Figure 6A:
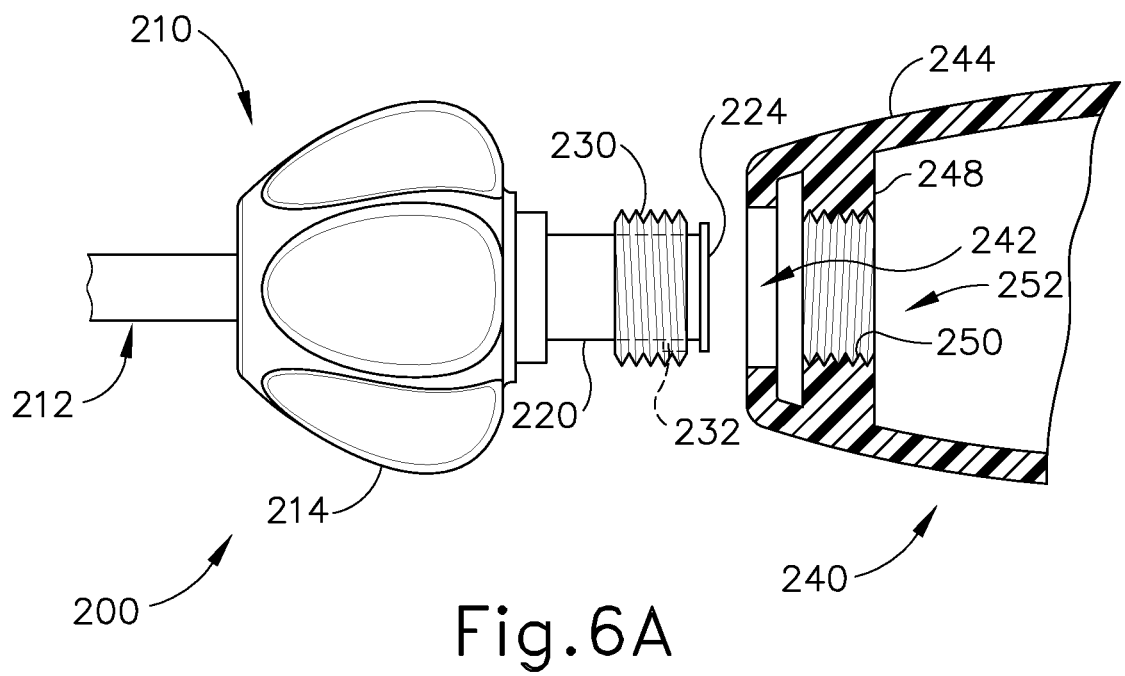
FIG. 6A depicts a side elevation view of a first exemplary coupling mechanism with a portion of a handle assembly in cross-section to show the interior thereof and showing a decoupled end effector assembly.
Figure 6B:
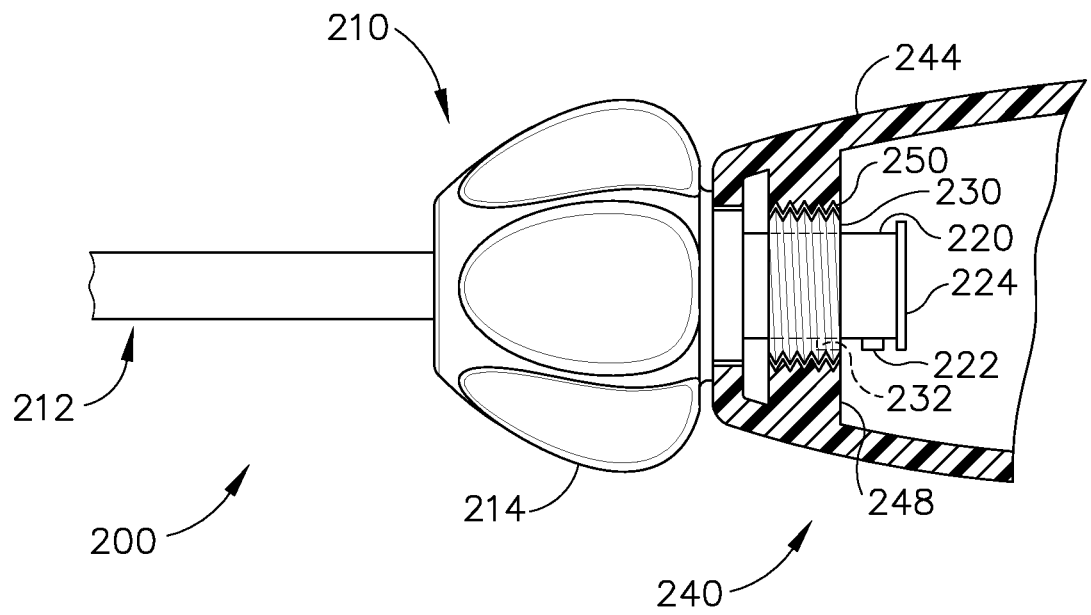
FIG. 6B depicts a side elevation view of the coupling mechanism of FIG. 6A showing the end effector assembly coupled to the handle assembly.

An exemplary coupling mechanism (200) comprises a threaded slip nut (230) disposed about a shaft (220) of an exemplary end effector assembly (210), shown in FIGS. 6A-6B. In the present example, end effector assembly (210) comprises a transmission assembly (212), a rotation knob (214), and a shaft (220) extending proximally relative to rotation knob (214). It should be understood that rotation knob (214) is merely optional and may be omitted. Rotation knob (214) is operable to rotate transmission assembly (212) relative to a handle assembly (240) and/or shaft (220). An end effector (not shown) is coupled to a distal end of transmission assembly (212). The end effector may include an ultrasonic end effector (80, 150), an RF end effector (180), and/or any other end effector or combination of end effectors as will be apparent to one of ordinary skill in the art in view of the teachings herein. Transmission assembly (212) is operable to communicate energy (e.g., ultrasonic vibrations, RF energy, and/or mechanical motion/force, etc.) from a source proximal to transmission assembly (212) to an end effector at the distal end of transmission assembly (212). In the instance of an ultrasonic end effector, such as end effector (80), an axial bore (not shown) through shaft (220) may permit mechanical coupling of transmission assembly (212) through shaft (220) to components within handle assembly (240), which may be configured in a similar manner to multi-piece handle assembly (60) described above. In the case of an RF end effector, such as end effector (180), the axial bore may permit a portion of transmission assembly (212) to extend at least partially through shaft (220). Transmission assembly (212) may include an inner slip ring connector that is electrically coupleable to a complementary slip ring connector on the interior of shaft (220) such that an electrical coupling from handle assembly (240) may be made to the end effector. In yet another alternative, a fluid coupling may also be made via the bore through shaft (220) and/or elsewhere on end effector assembly (210).

In the present example, a threaded slip nut (230) is slidably disposed about shaft (220). Threaded slip nut (230) includes a keyway (232) (shown in phantom) at a proximal end of threaded slip nut (230). It should be understood that keyway (232) may alternatively be located on a distal end of threaded slip nut (230). Keyway (232) of the present example only partially extends through threaded slip nut (230), though keyway (232) may alternatively extend completely through threaded slip nut (230). As shown in FIGS. 6A-6B, keyway (232) is configured to receive a keyed portion (222) of shaft (220). In the present example, keyed portion (222) of shaft (220) is located near a proximal end of shaft (220) and extends outwardly from shaft (220), though it should be understood that keyed portion (222) may alternatively be located distally near rotation knob (214) or at a midpoint of shaft (220). In one merely alternative example, keyed portion (222) may be slidable relative to shaft (220), such as by actuation of a slider to slide keyed portion (222) into keyway (232). Shaft (220) further comprises a proximal flange (224) located on the proximal end of shaft (220) and sized to prevent threaded slip nut (230) from sliding proximally off of shaft (220). As will be described below, keyed portion (222) is insertable into keyway (232) when a user desires to thread threaded slip nut (230) into internal threading (250) of handle assembly (240). Threaded slip nut (230) of the present example may then be slid distally on shaft (220) to disengage keyed portion (222) from keyway (232), thereby permitting shaft (220), rotation knob (214), and/or transmission assembly (212) to rotate freely relative to threaded slip nut (230) and/or handle assembly (240).

In some instance threaded slip nut (230) may be slidably disposed on an inner tube, such as an inner tubular actuating member described above. In such a configuration, threaded slip nut (230) may be configured to thread into a yoke, such as trigger yoke (185) described in U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein. A blade, such as blade (82) described above, may be coupled to a transducer, such as transducer (100) described above. The inner tubular actuating member may be actuated via the coupling of threaded slip nut (230) to the yoke. Accordingly, a clamp arm, such as clamp arm (84) described above, may be operable to clamp tissue against the blade.

In the present example, handle assembly (240) is shown having a distal aperture (242) formed within a casing (244) and configured to receive shaft (220) and threaded slip nut (230) of end effector assembly (210). Handle assembly (240) may further be configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, or of U.S. Pat. No. 6,500,176, entitled "Electrosurgical Systems and Techniques for Sealing Tissue," issued Dec. 31, 2002, the disclosures of which are incorporated by reference herein, and/or in any other suitable fashion. In the present example, handle assembly (240) includes a member (248) having internal threading (250) disposed about a member aperture (252). Internal threading (250) and threaded slip nut (230) are configured to thread together to secure end effector assembly (210) to handle assembly (240).

As shown in the sequence of FIGS. 6A-6B, threaded slip nut (230) of the present example is slid proximally such that keyed portion (222) of shaft (220) engages keyway (232) of threaded slip nut (230). With the rotational freedom of threaded slip nut (230) restricted by the engagement of keyed portion (222) and keyway (232), a user then threads threaded slip nut (230) into internal threading (250) of handle assembly (240). For instance, an L-shaped spacer tool may be used to urge threaded slip nut (230) proximally on shaft (220) against flange (224) while the user threads threaded slip nut (230) into internal threading (250). Alternatively, a user may manually urge threaded slip nut (230) proximally. Further still, a slider, as noted above, may engage a portion of threaded slip nut (230) to urge threaded slip nut (230) proximally. Of course, still other methods of urging threaded slip nut (230) proximally to engage keyed portion (222) and keyway (232) will be apparent to those of ordinary skill in the art in view of the teachings herein. For instance, a spring (not shown) may be disposed about shaft (220) distally of slip nut (230) and proximally of rotation knob (214), thereby biasing slip nut (230) proximally such that keyway (232) is engaged with keyed portion (222). When the user desires to rotate end effector assembly (210), the user grasps rotation knob (214) and pushes end effector assembly (210) proximally until keyed portion (222) disengages from keyway (232).

Once threaded slip nut (230) has been sufficiently threaded into internal threading (250) (for instance, a torque limiting tool may be used), end effector assembly (210) is slid proximally to disengage keyed portion (222) from keyway (232). End effector assembly (210) may be manually slid distally or, in one alternative, a spring (not shown) located between flange (224) and threaded slip nut (230) may urge end effector assembly (210) distally. In the instance of an ultrasonic instrument, shaft (220) of end effector assembly (210) may be threaded onto a horn of a transducer, such as transducer (100) described above. Such threading may occur prior to, contemporaneously with, or after the threading of threaded slip nut (230) into internal threading (250). Alternatively, in the instance of an RF instrument, shaft (220) may be coupled to one or more electrical connectors (not shown) to couple the end effector to a power source. As shown in FIG. 6B, end effector assembly (210) is effectively longitudinally secured to handle assembly (240) while permitting rotational movement of shaft (220), rotation knob (214), and/or transmission assembly (212). A user may then use the assembled surgical instrument for a procedure. When the user desires to decouple end effector assembly (210) from handle assembly (240), the user pulls end effector assembly (210) distally until keyed portion (222) of shaft (220) engages keyway (232) of threaded slip nut (230). Alternatively, the L-shaped spacer tool may be wedged between threaded slip nut (230) and rotation knob (214) to urge threaded slip nut (230) proximally. With keyed portion (222) and keyway (232) engaged, the user may then unscrew threaded slip nut (230) from internal threading (250), thereby decoupling end effector assembly (210) from handle assembly (240). A user may then couple a new end effector assembly (210) to handle assembly (240).

Of course other configurations for coupling mechanism (200) will be apparent to one of ordinary skill in the art in view of the teachings herein. For instance, threaded slip nut (230) may be located between flange (224) and another annular flange (not shown) of shaft (220). In this example, keyed portion (222) may be actuated radially outward from an initial position within a recess (not shown) of shaft (220) to a position where keyed portion (222) engages keyway (232) of threaded slip nut (230). For instance, keyed portion (222) may be actuated by a cam member coupled to a slider located on transmission assembly (212) and/or rotation knob (214). As will become apparent from the previous and later disclosures herein, various other electrical and/or mechanical coupling mechanisms and/or features may be used to substitute coupling mechanism (200), to modify coupling mechanism (200), or to combine with coupling mechanism (200).

V. Exemplary Information Transmission System

Figure 7:
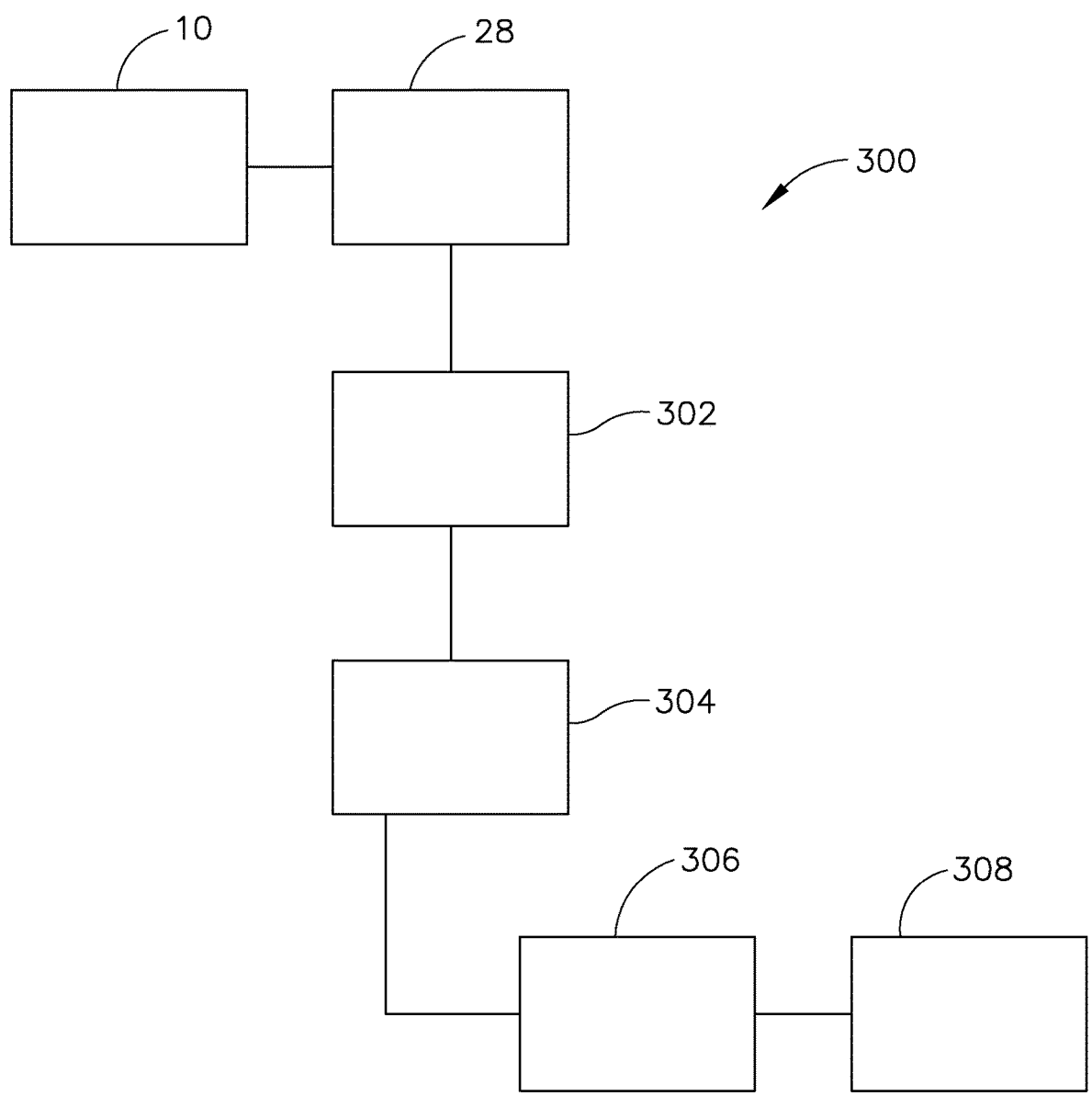
FIG. 7 depicts a schematic view of an exemplary information transmission system.

FIG. 7 shows a schematic view of an information transmission system (300) using device (10) to transmit information. It should be understood that various kinds of devices or instruments (10, 24, 101, 159) may be used in system (300) alongside removable end effectors (16, 80, 150, 180), respective transmission assemblies (70, 102, 170), and reusable handle assemblies (60, 120, 160) where it may be useful to change between various shaft lengths and/or types, as described above. Device (10) is shown as connected to generator (28), as described above, though generator (28) may be incorporated into device (10) or omitted in some versions. Sensor (20) in device (10), which may be included in any of instruments (24, 101, 159), may gather information regarding use of device (10) during a surgical procedure on a patient. Such information may be transmitted to generator (28), which then transmits the information via a secure gateway (302) to a secure server (304). Gateway (302) of the present example includes Secure Web Gateway (SWG) technology combining features such as anti-malware, URL filtering, web content filtering, bandwidth management, application control, and/or caching capabilities in order to secure, monitor, and control traffic between generator (28) and server (304), regardless of whether such traffic is encrypted or not. Server (304), which may be a secure server outside a hospital network, communicates the information via a secure web interface (306) to a unique patient file (308). Patient file (308) includes patient history specific to the first patient on whom device (10) was used during the surgical procedure from which information was collected and transmitted. The particular device (10) and components used on the first patient may be, for example, tracked and entered into patient file (308) via the system shown in FIG. 7. Information may be shared to patient file (308) directly after use of device (10) in the associated surgical procedure performed on the first patient. To the extent that a hospital desires to track patient care throughout an entire experience associated with a patient, including but not limited information such as the types of tools, services, and materials that were used on or for a patient during that patient's hospital experience, system (300) assists with this goal by providing desired information regarding device (10) used with a patient during a particular surgical procedure. By tracking information such as amount of time a device such as device (10) and its attached and/or removable components were used on a patient along with electrical characteristics associated with such use, and the types of device and/or device components used, a cost may be calculated based on the tracked information. Further, by tracking such information and data monitoring, analysis and recommendations for future surgical improvements may be obtained from the tracked procedure data to improve outcomes of and to build best practices for similar future surgeries. Hospitals using system (300) may control what type of data tracked during use of device (10) is associated with a specific patient that device (10) was used upon during a surgical procedure, and thus which data is viewable in patient file (308). System (300) transmits information via a secure process as described below.

Figure 8A:
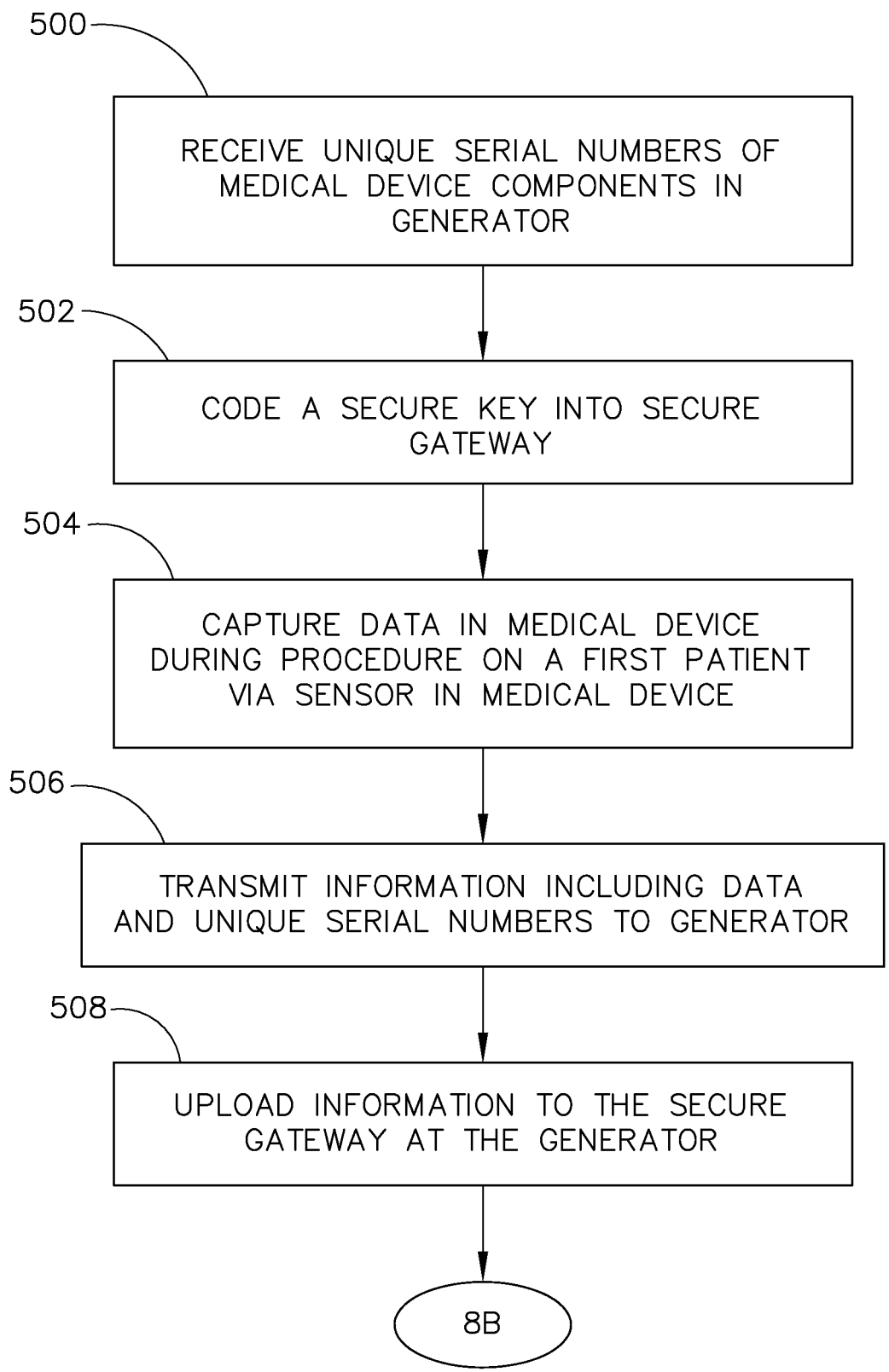
FIG. 8A depicts a first portion of a flowchart showing an exemplary use of the information transmission system of FIG. 7.
Figure 8B:
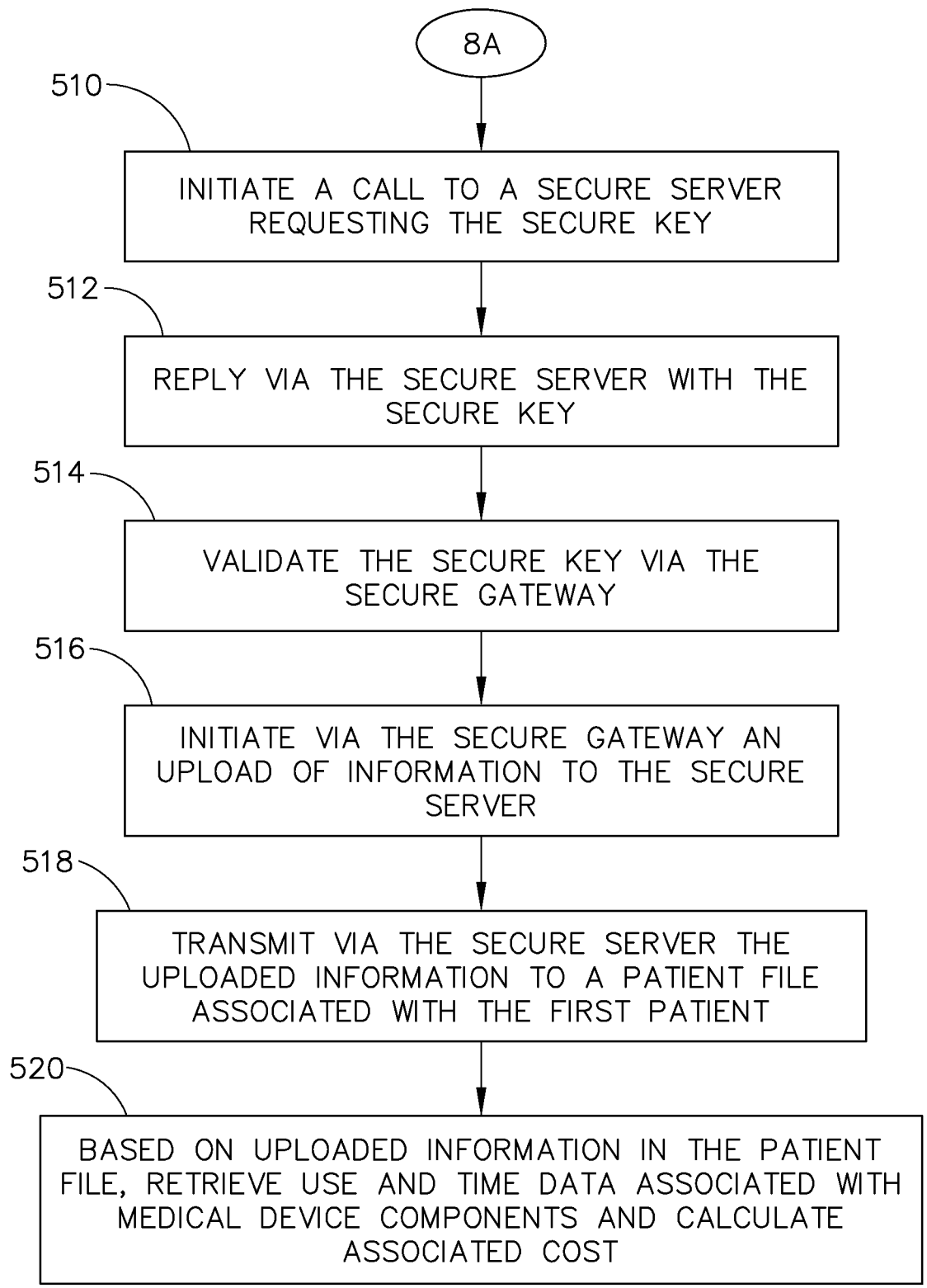
FIG. 8B depicts a second, continued portion of a flowchart showing an exemplary use of the information transmission system of FIG. 7.

FIGS. 8A-8B show an exemplary process that may be carried out using system (300). Unique serial numbers may be associated with particular types of instruments (10, 24, 101, 159) and/or medical device components, such as removable end effectors (16, 80, 150, 180), and respective transmission assemblies (70, 102, 170), and handle assemblies (60, 120, 160). Each unique serial number of device (10), for example, and components associated with device (10), is received (500) by generator (28). For example, such data may be transmitted to and received by generator (28) via a wired or wireless connection, may be manually inputted into a user interface in communication with generator (28), and/or may be automatically registered by generator (28) via a receiver in communication with generator (28). For ease of reference, regarding use with system (300), when device (10) is referenced alongside its components, it is understood that any of devices or instruments (10, 24, 101, 159) alongside respective removable end effectors (16, 80, 150, 180), and respective transmission assemblies (70, 102, 170), and respective handle assemblies (60, 120, 160) may be used in place of device (10) and its components. Additionally or alternatively, generator (28) may be removed from system (300) and information from sensor (20) of device (10), or other instruments such as instrument (159), for example, may be transmitted wirelessly and/or via a wired communication to secure gateway (302).

Information such as the type of device (10) and type of end effector (16) used, or that of any of the instruments, end effectors, transmission assemblies, and/or handle assemblies within the present disclosure, and the amount of time such components were used during a surgical procedure on a patient are transmitted via system (300) to server (304). System (300) may also transmit information indicating the type of surgical procedure to server (304). Other suitable types of information that may be transmitted to server (304) will be apparent to one of ordinary skill in the art in view of the teachings herein. As shown in FIG. 8, unique serial numbers of medical device components used or to be used in a surgical procedure, are received (500) in generator (28). A security or secure key is or has been coded (502) into secure gateway (302). The medical device components are then used on a first patient during a surgical procedure. Data is captured (504) in device (10), for example, during the surgical procedure on the first patient via sensor (20) in device (10). As described above, such data may include a sensed temperature at end effector (16), a determined oscillation rate of end effector (16), the impedance of tissue encountered by end effector (16) and/or other properties of such tissue, motions of end effector (16) during a surgical procedure (e.g., when sensor (20) includes an accelerometer), and/or other data as will be apparent to one of ordinary skill in the art in view of the teachings herein. Information including the captured data and the unique serial numbers associated with the used device (10) and end effector (16), for example, is transmitted (506) to generator (28). Generator (28) may be connected via, for example, a USB port, ethernet, or other wired or wireless connection to secure gateway (302) in a one-way or two-way connection. The gathered information is thereby uploaded (508) to secure gateway (302) via generator (28). It should be understood that any step within steps (500-508) may be performed at any suitable time. For instance, step (508) may be carried out through a continuous data stream throughout the surgical procedure. Alternatively, step (508) may be carried out after the procedure is complete. Other time frames and relationships will be apparent to one of ordinary skill in the art in view of the teachings herein.

As shown in FIG. 8B, after the surgical procedure is compete, a call is initiated (510) to secure server (304) to request the previously coded secure key. Server (304) replies (512) to the call request with the previously coded secure key. The secure key is validated (514) via secure gateway (302) after being received. Upon successful completion of the secure key validation, an upload of information to secure server (304) is initiated (516) via secure gateway (302). The uploaded information is transmitted (518) via secure server (304) to patient file (308) associated with the first patient that underwent the surgical procedure using device (10) and end effector (16). In some instances a cost is determined (520) based on the transmitted, uploaded information in patient file (308), amount of time used and data regarding use of device (10) and end effector (16), and other device components, and/or other information. For instance, a dollar amount may be associated with minutes of use for device (10), for an amount of voltage used via a connection between generator (28) and device (10) for application on tissue of the first patient during the surgical procedure, total energy used by device (10), total current used by device (10), number of activations of device (10), and/or various other parameters, including various combinations of parameters. The retrieved information may be tallied and a pre-set calculation may be applied to the retrieved information to generate an overall cost of use associated with device (10) during the surgical procedure on the first patient. The tallied cost may be stored in patient file (308) and displayed on, for example, a computer monitor or other user information or printed on one or more reports generated from patient file (308). A hospital may track costs associated across various patients with devices and/or components having certain serial numbers to analyze results and view which types of devices and/or components may be more costly than others or might be desirably used in certain types of surgeries in a cost-effective and time-effective manner.

The tallied cost may also be submitted to an outside server (304) as an invoice that the hospital might pay to one or more vendors or manufacturers of device (10), end effector (16), and/or other components of device (10). Server (304) also may play the function of notifying a hospital information technology system that new data has been logged into a patient file (308) along with information regarding the time of receipt of the logged information and other suitable information as apparent to one of ordinary skill in the art in view of the teachings herein. Of course, the instrument usage data need not necessarily be used for establishing usage costs or controls. For instance, usage data may be used as a measure of surgical time, surgeon/operator performance, efficiency, effectiveness, etc. Other suitable ways in which instrument usage data might be used will be apparent to one of ordinary skill in the art in view of the teachings herein.

VI. Exemplary Sensor to Track Instrument Usage Characteristics

FIGS. 9-12 show graphical views of sample instrument usage characteristics trackable on device (10) during a surgical procedure on a patient, for example, via sensor (20) of device (10). Sensor (20) in an example may track a technique that a surgeon uses on device (10) during the procedure. Feedback from sensor (20), for example, may be transmitted via a wired or wireless connection to a receiving device such as server (304) or other suitable device, such as a computer or smartphone. Software programs can then be used to analyze the transmitted data for use by the surgeon, the Operation Room ("OR") staff, biomedical researchers, or others, such as in a manner as described in accordance with the teachings of U.S. patent application Ser. No. 13/276,725, issued as U.S. Pat. No. 9,095,346 on Aug. 4, 2015, the disclosure of which is incorporated by reference herein.

Sensor (20) may comprise, for example, a piezoelectric accelerometer, a gyroscope, a pressure sensor, a force transducer, and/or other suitable type of sensor as apparent to one of ordinary skill in the art in view of the teachings herein. It should be understood that device (10) may include more than one type of integral sensor (20). Sensor (20) may be operable in accordance with the teachings of U.S. patent application Ser. No. 13/276,660, issued as U.S. Pat. No. 9,364,279 on Jun. 14, 2016, the disclosure of which is incorporated herein. For example, a pressure sensor may be built into trigger (18) of device (10). The pressure sensor may comprise an electronic pressure sensor, or pressure transducer, converting pressure into an analog electrical signal. Such pressure transducers may utilize force collectors such as a diaphragm to measure strain or deflection due to an applied force over a space. Force collector types may include but not be limited to a piezoresistive strain gauge, capacitive strain gauge, electromagnetic strain gauge, piezoelectric strain gauge, and/or optical strain gauge. Various suitable forms that such gauges may take will be apparent to those of ordinary skill in the art in view of the teachings herein. Similarly, various suitable ways in which such strain gauges may be incorporated into trigger (18) will be apparent to those of ordinary skill in the art in view of the teachings herein.

Sensor (20) may be disposed in any of instruments (10, 24, 101, 159) and in various locations within instruments (10, 24, 101, 159), such as in removable end effectors (16, 80, 150, 180), and/or respective transmission assemblies (70, 102, 170), and/or handle assemblies (60, 120, 160). Removable end effectors (16, 80, 150, 180), and/or respective transmission assemblies (70, 102, 170), attachable to handle assemblies (60, 120, 160) are referable to as "Apps" in the present disclosure. Sensor (20) may be disposed in, for example, a removable App that is attachable to a handle portion of device (10).

It should be understood that sensor (20) may take a variety of additional or alternative forms. For instance, sensor (20) may be operable to measure the acoustic impedance of device (10). In addition or in the alternative, sensor (20) may be operable to measure electrical impedance of tissue. Furthermore, sensor (20) may comprise a displacement measuring device giving feedback on a position of a clamp arm of end effector (16) (e.g., indicating whether the clamp arm is in an open position, closed position, or somewhere between). Sensor (20) may also comprise one or more thermal sensors disposed within the clamp arm of the end effector to register a clamp arm temperature and/or a tissue temperature. Sensor (20) may also comprise a pressure sensor disposed in the clamp arm of end effector (16) to measure the pressure applied to tissue by the clamp arm and an opposing blade of end effector (16). Sensor (20) may additionally be a combination of two or more of the above-described sensors. For example, one or more sensors (20) may be operable to provide information regarding both clamp force as well as clamp arm position. Other suitable forms that sensor (20) may take will be apparent to those of ordinary skill in the art in view of the teachings herein.

After device (10) is used in a procedure and/or during use of device (10) in a procedure, for example, information may be transmitted via a wireless or wired communication to generator (28), to a smartphone, and/or to a computer, as described above. If transmitted via a wired connection, the connection may stem from the used App, the handle portion of device (10), and/or generator (28) attached to device (10). Transmitted information may be uploaded to server (304) and be used in information transmission system (300) as described above. In addition to information gathered by sensor (20), such transmitted information may include information from generator (28) relating to generator (28) operating parameters during the surgical procedure, information relating to the type of surgical procedure (e.g., manually inputted by a user), and/or any other type of information as will be apparent to one of ordinary skill in the art in view of the teachings herein. Uploaded information may be viewable on a user interface on a computer, for example, and may be used for data analysis (such as analysis of electrical characteristics received from generator (28) after a surgical procedure). FIGS. 9-12 show examples of data and information on a user interface that users may review and analyze after transmission of such information as described above.

Figure 9:
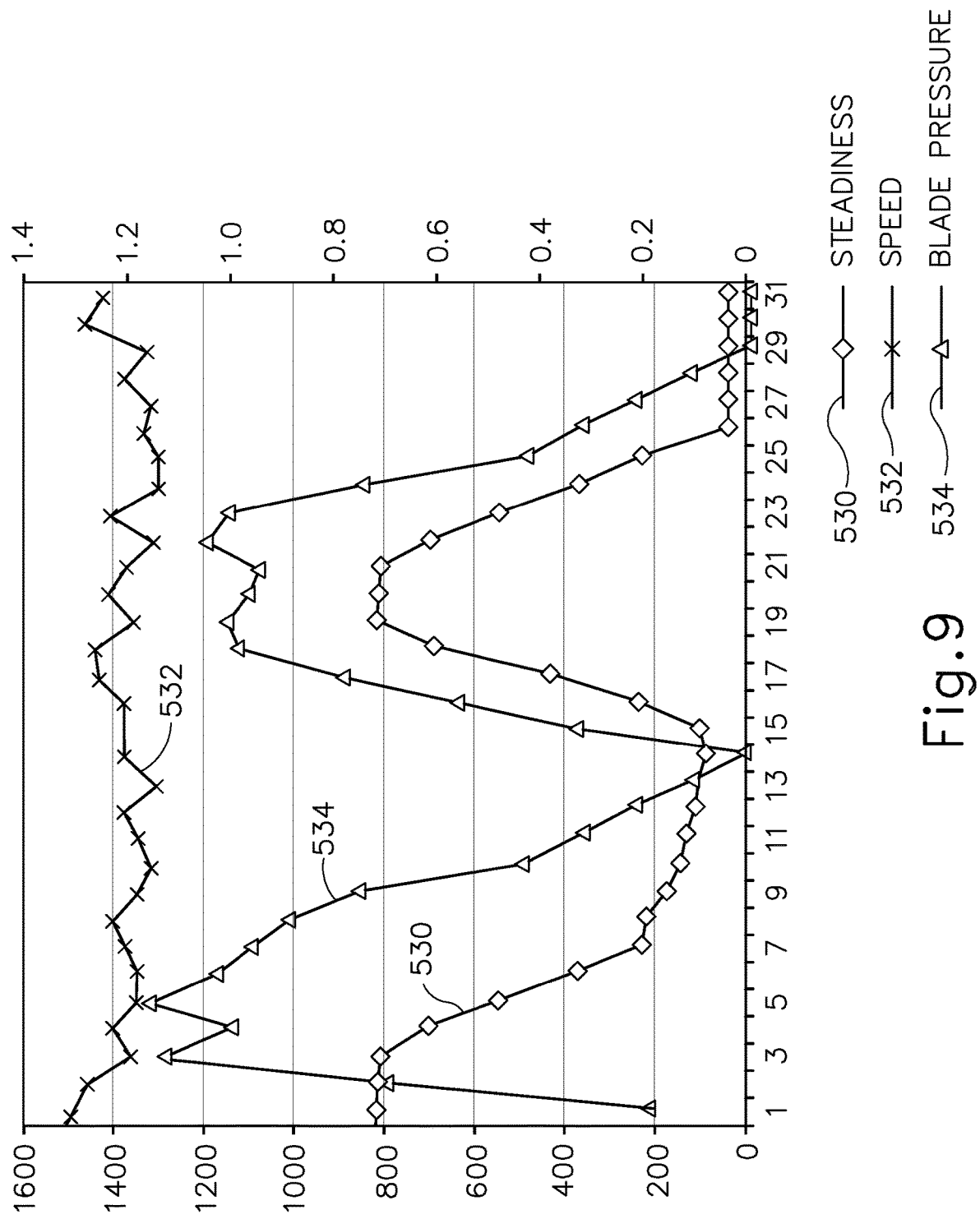
FIG. 9 depicts a graphical view of data transmitted from an exemplary sensor of an exemplary medical device.

FIG. 9 shows a view of data retrieved from sensor (20) in a used App and/or handle portion of device (10), for example. The data in this example includes information regarding steadiness (530), speed (532), and blade pressure (534) mapped out over an x-value of time in seconds. The left side y-value shows units of microns of movement per second, indicating steadiness (530) of device (10); and the right side y-value shows units of pounds of force, indicating blade pressure (534). As shown in FIG. 9, over the time device (10) was used in a sample surgical procedure, the surgeon using device (10) used a fairly constant speed (532) with device (10), applied about two cycles of built up and reduced pressure (534) on end effector (16) of device (10) against the operated-upon tissue, and has a steadiness (530) that fairly paralleled the blade pressure (534) applied against the tissue, with steadiness (530) building when pressure (534) built and dropping when pressure (534) dropped. Such data may be interpreted to indicate that, as blade pressure (534) increases, the ability to maintain steadiness (530) of device (10) decreases.

Figure 10:
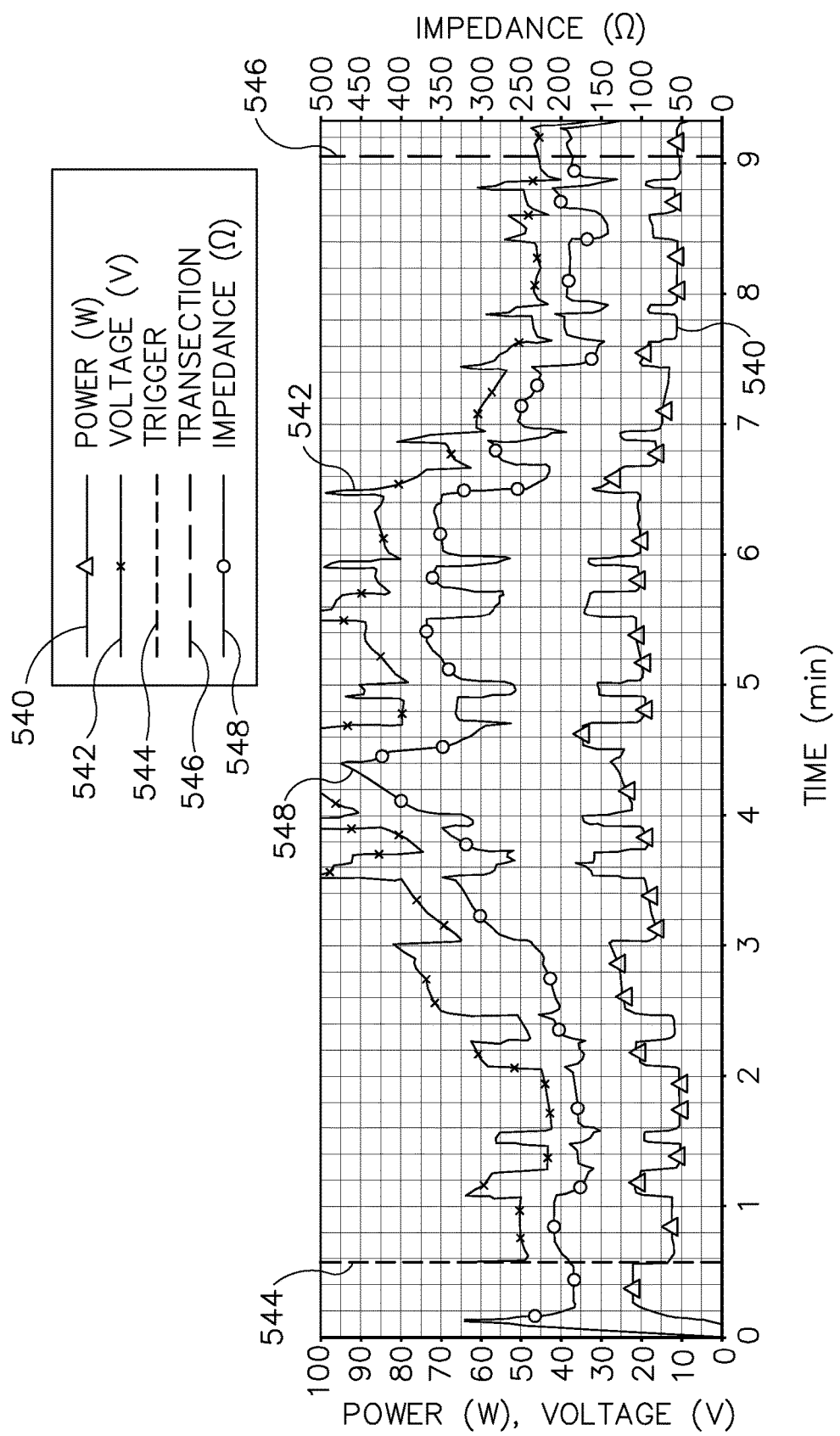
FIG. 10 depicts a first graphical view of electrical characteristics associated with a generator and a medical device during a procedure.
Figure 11:
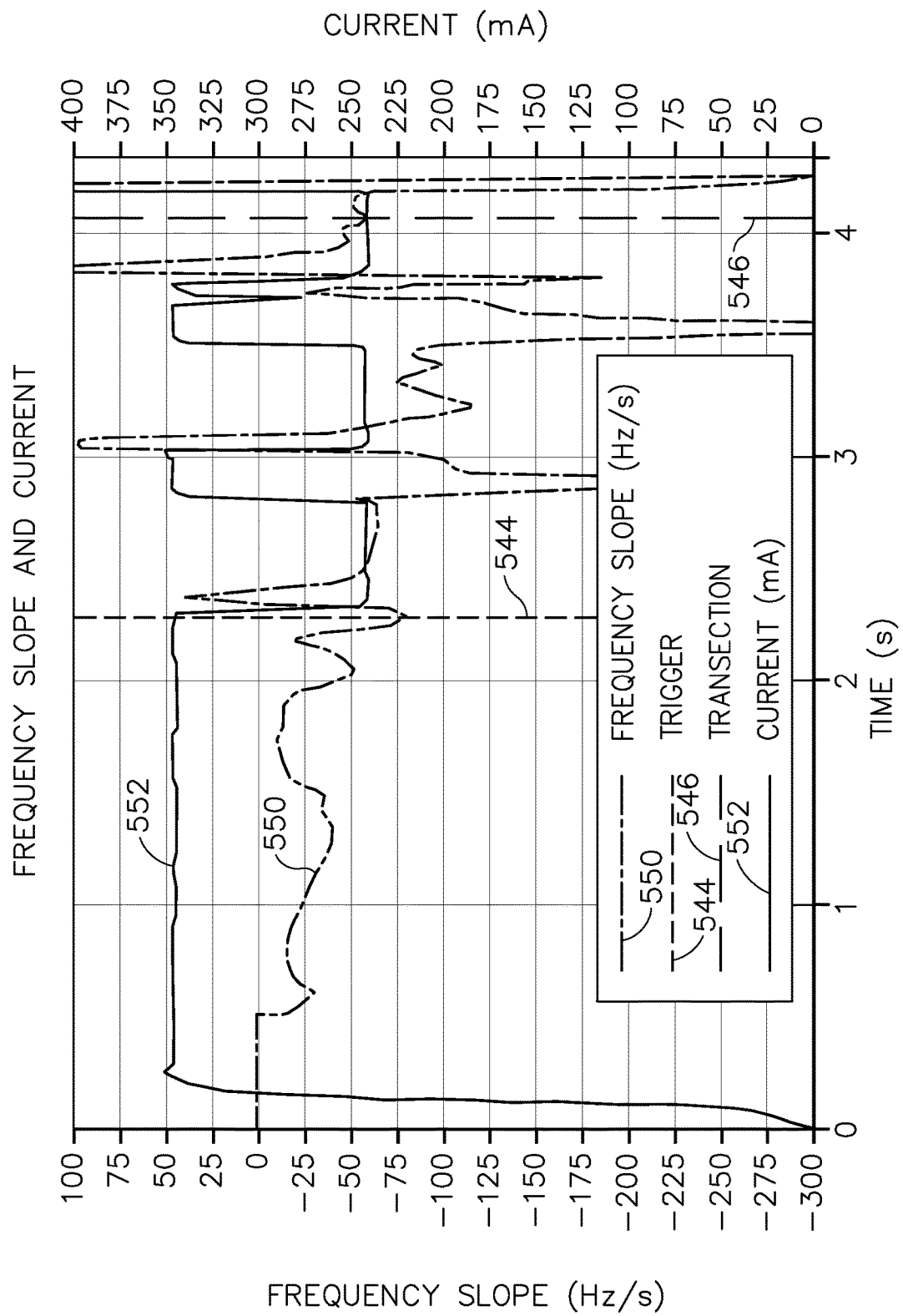
FIG. 11 depicts a second graphical view of electrical characteristics associated with a generator and a medical device during a procedure.
Figure 12:
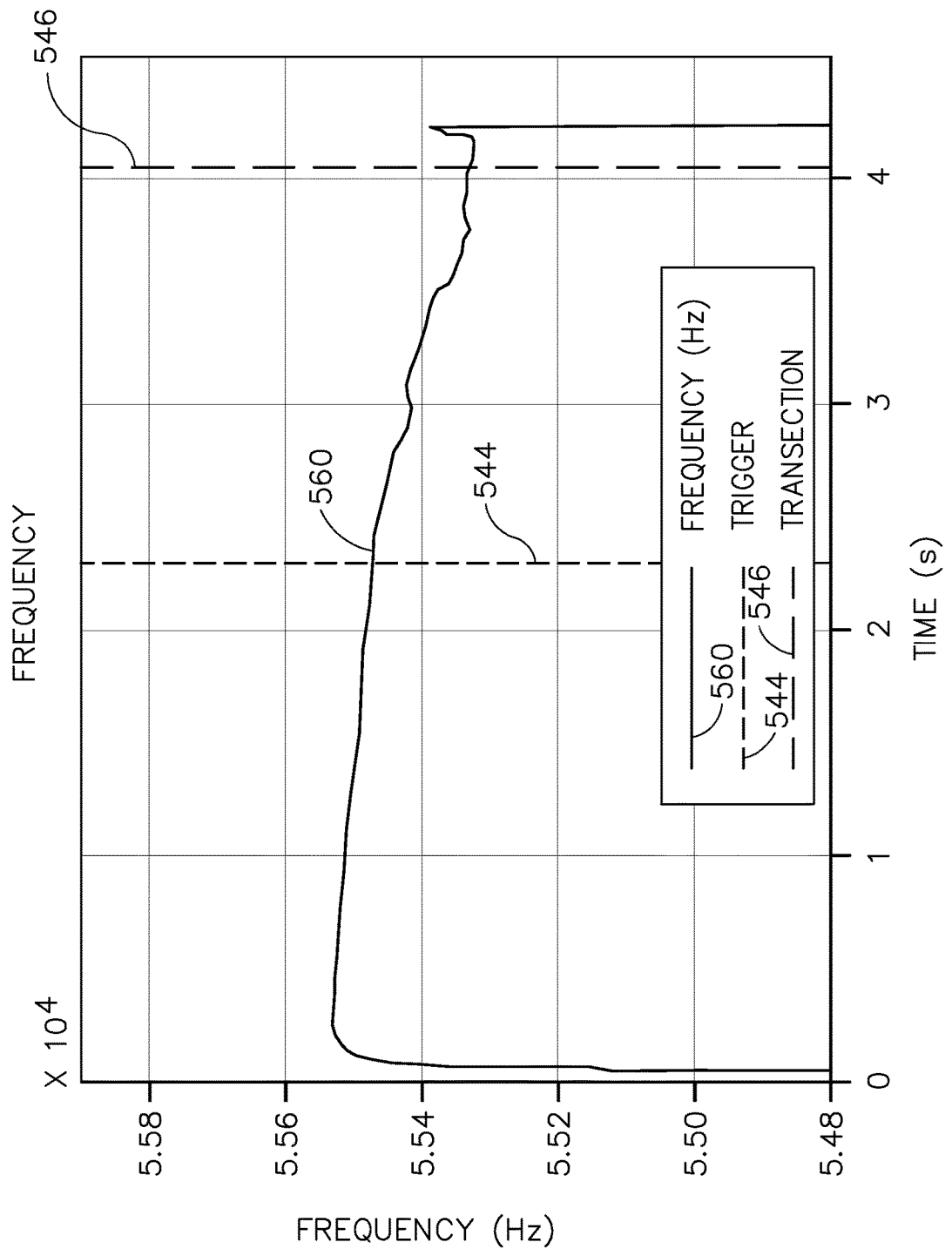
FIG. 12 depicts a third graphical view of electrical characteristics associated with a generator and a medical device during a procedure.

FIG. 10 shows a view of electrical characteristics data retrieved from generator (28) after a surgical procedure, for example, via sensor (20) and/or generator (28). The x-value on the graphs measures time in minutes. The left side y-value measures both power (540) measured in Watts (W) and voltage (542) measured in Volts (V), and the right side y-value measures tissue impedance (548) in units of Ohms (Q). Impedance correlates to an amount of resistance to current in tissue (such that an increased impedance reduces the flow of current). For instance, sensor (20) may be used to sense tissue impedance. The application of trigger (18) of device (10) is shown by line (544) at a first time around 30 seconds into the procedure. The transection of operated upon tissue via end effector (16), for example, is shown by line (546) about 9 minutes into the procedure. FIGS. 11-12 also depict graphs indicating an application of trigger (18), shown via line (544), and a transection of operated upon tissue by end effector (16), shown via line (546).

Power (540), voltage (542), and impedance (548) are fairly consistent in the terms of use as each appears to respectively rise and fall in respective measured units alongside similar increases and decreases of unit measurements the other electrical characteristics. For example, as power increases, voltage tends to increase, and impedance tends to increase at relatively similar rates. Thus, when an increased voltage (542) is being applied to device (10) from, for example, generator (28), FIG. 10 appears to indicate that a corresponding increase in impedance (548) reduces the flow of current to the operated upon tissue. Such data might be interpreted to indicate why tissue transaction times might be slower in certain settings. Such data could further be interpreted indicate the type of tissue being transected.

FIG. 11 shows a view of other electrical characteristics data retrieved from generator (28) after a surgical procedure, for example, via sensor (20) and/or generator (28). In particular, FIG. 11 analyses the frequency slope and current characteristics retrieved from generator (28). The x-value on the graphs measures time in seconds. The left side y-value depicts frequency slope (550) measured in Hertz per Second (Hz/s), and the right side y-value measures current (552) measured in milli-Amps (mA). Line (544) shows that trigger (18) of device (10), for example, was applied at about some seconds past a 2 minute mark on the graph and the transection to the operated upon tissue by end effector (16) occurred at about just past the 4 minute mark. Generally, when trigger (18) was applied, current (552) dropped. Between lines (544, 546), when current (552) dropped or decreased, frequency slope (550) tended to rise or increase, and when current (552) increased, frequency slope (550) tended to decrease.

FIG. 12 shows a view of other electrical characteristics data retrieved from generator (28) after a surgical procedure, for example, via sensor (20) and/or generator (28). In particular, FIG. 12 analyses the frequency characteristics retrieved from generator (28). The x-value on the graphs measures time in seconds. The left side y-value depicts frequency (560) measured in Hertz (Hz). Similar to FIG. 11, line (544) shows that trigger (18) of device (10), for example, was applied at about some seconds past a 2 minute mark on the graph and the transection to the operated upon tissue by end effector (16) occurred at about just past the 4 minute mark. Generally, between the time trigger (18) was applied and the transaction occurred via device (10), frequency (560) dropped.

The graphs may assist a user with reviewing and analysis of the data associated with a specific surgery on a specific patient. Through a web interface or other type of graphical user interface, a user may mark such data with note, such as how tired a surgeon felt on a particular day for example, or the number of assistants in the room for the particular, tracked surgery, as well as the equipment available for the surgical procedure. By way of example only, a user may annotate graphs in accordance with at least some of the teachings of U.S. Patent Appl. Publ. No. 2011/0172687, entitled "Telemetry Device with Software User Input Features," published Jul. 14, 2011, issued as U.S. Pat. No. 8,852,118 on Oct. 7, 2014, the disclosure of which is incorporated by reference herein. A software application tool may be utilized to further export and analysis the data to determine, for example, what the source of a user's habits might be, and/or whether a user tends to move a blade of an end effector, such as end effector (16), around more than desired when transecting a high-risk area (e.g., an area surrounded with substantially small blood vessels). By way of example only, the data may also be used to determine if the surgeon's diet, exercise, mental state, and/or other conditions affect the surgeon's steadiness or overall timing of a surgical procedure (or segment of a surgical procedure). Other suitable ways in which the above-described types of data may be used will be apparent to one of ordinary skill in the art in view of the teachings herein.

VII. Exemplary Calibration Kit

Figure 13A:
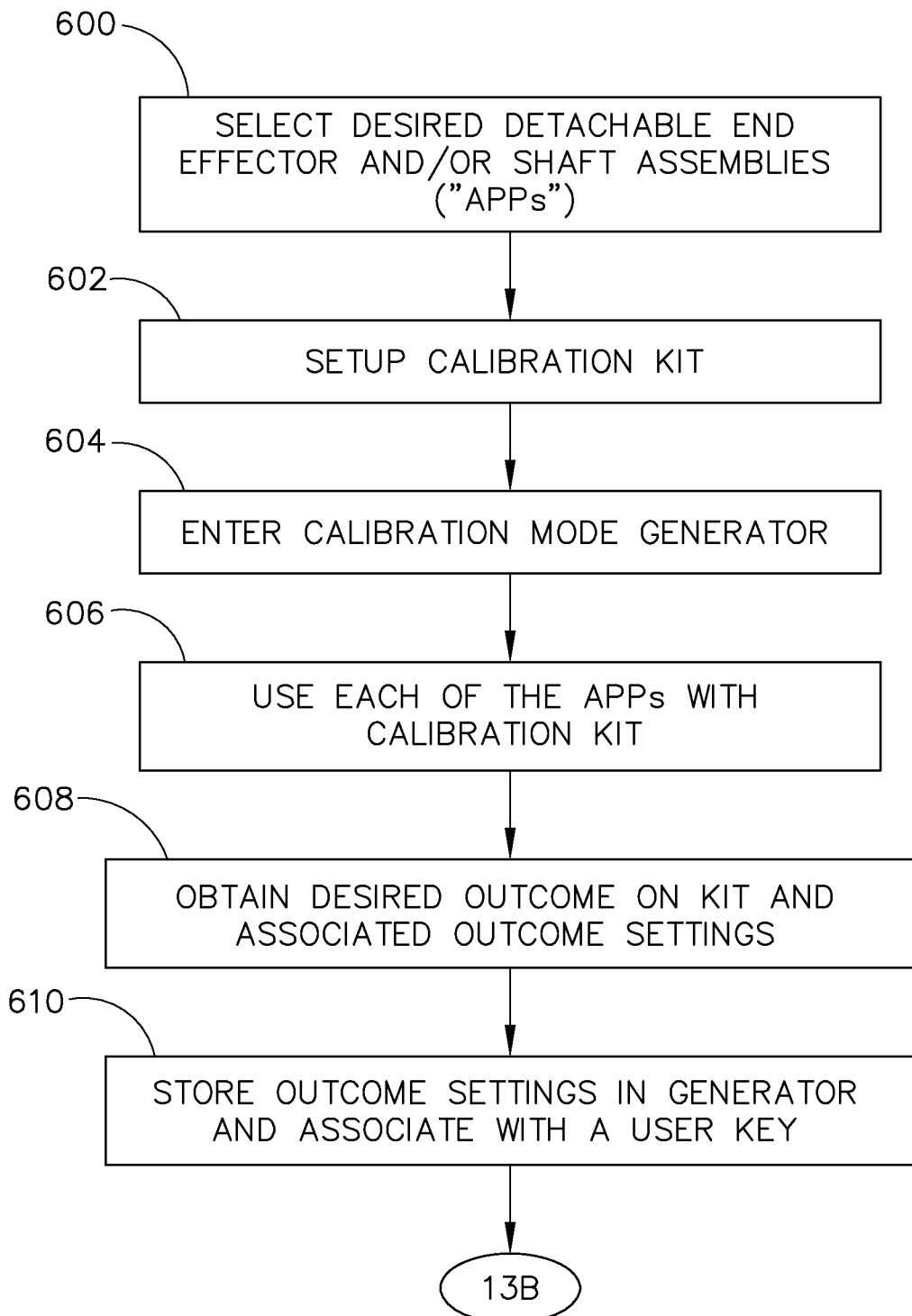
FIG. 13A depicts a first portion of a flowchart showing an exemplary use of an exemplary calibration kit with a medical device.
Figure 13B:
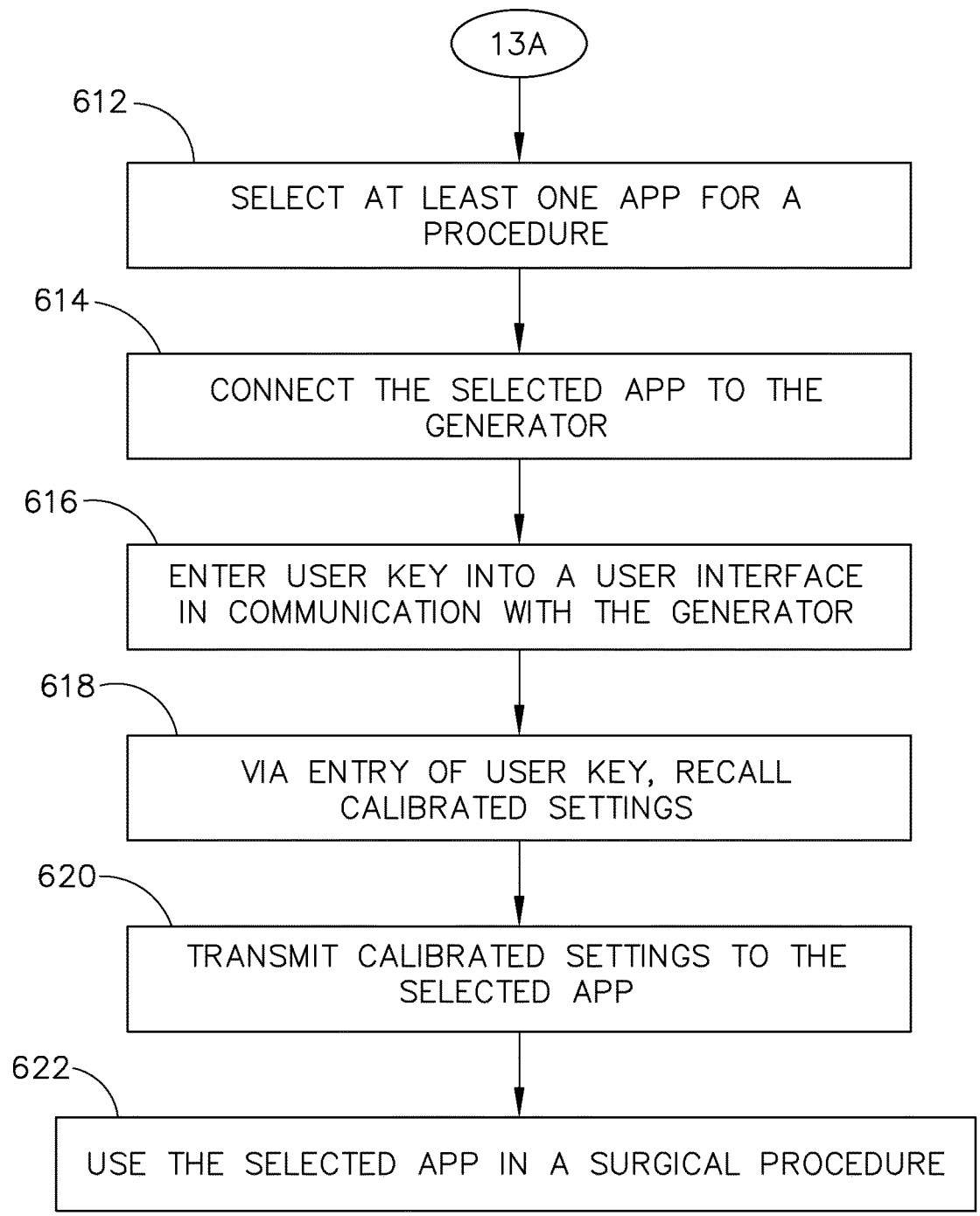
FIG. 13B depicts a second, continued portion of a flowchart showing an exemplary use of an exemplary calibration kit with a medical device.

FIGS. 13A-13B depict a process of using a calibration kit to set and store outcome settings which may be applied to at least one selected App for a device (10), for example, during a procedure. This process may be used to learn and account for unique usage idiosyncrasies for each surgeon, such as abnormal surgical techniques/tendencies, to promote consistent surgical results. Desired datable end effectors and/or shaft assemblies, described above as Apps, are selected (600) by a user. Additionally, a calibration kit is setup (602). The calibration kit may include, for example, synthetic tissue models having known parameters and characteristics, tissue such as pork belly or other suitable testable organic and/or synthetic tissue, sample vessels from suitable testable sources (such as, for example, a pig), and other suitable testable parts from a testable source, as well as other suitable testable materials that may be organic and/or synthetic. The calibration kit includes various materials that assist to gather data to test a surgeon's usage behavior and preferences with a device (10), for example, on the test material before testing the usage on a patient during a surgical procedure. Certain various parameters may be tracked and calibrated, such as a preferred force the surgeon desires to apply, average speeds the surgeon tends to use, and/or other parameters as will be apparent to one of ordinary skill in the art in view of the teachings herein. In the present example, generator (28) provides selection between a calibration mode and at least one surgical procedure mode.

FIG. 13A shows that a calibration mode including such parameters to track, for example, is entered (604) on generator (28). Each of the selected Apps are used (606) with the calibration kit by the surgeon to establish the surgeon's personally calibrated parameter settings. For example, a surgeon uses a selected App on organic pig tissue that may be included in the calibration kit, utilizing the App with device (10) to cut, transect, and seal the pig tissue and internal vessels and retrieve usage data from the test procedure on the pig tissue. For instance, the user may delete data associated with unsuccessful testing on the tissue/model provided in the kit, saving only data associated with successful testing. In addition or in the alternative, generator (28) can automatically adjust its own operating parameters during the calibration process in an attempt to achieve surgical success in the testing despite any abnormal surgical techniques/tendencies displayed by the surgeon. The desired outcome centered on these parameters are obtained (608) via use of the calibration kit as well as a set of associated outcome settings or parameters. The obtained outcome settings (610) are stored in generator (28) and are associated with a user key. The obtained outcome settings (610) may also include data gathered in accordance with other teachings herein (e.g., from sensor (20)). Based on data collected during the calibration procedure shown in FIG. 13A, generator (28) is able to establish compensatory operating parameters to compensate for surgeon tendencies. For instance, if the calibration process shows that the surgeon tends to apply an abnormally high amount of force to tissue, generator (28) may know to reduce power to avoid unintended/adverse tissue damage. Other ways in which operating parameters of generator (28) may be adjusted based on surgeon usage idiosyncrasies will be apparent to one of ordinary skill in the art in view of the teachings herein.

FIG. 13B shows steps that may be carried out after generator (28) has been calibrated based on the particular surgeon's unique usage idiosyncrasies. In particular, FIG. 13B shows that at least one App is selected (612) for use in a surgical procedure by, for example, the surgeon. The selected App is connected (614) to the generator (28). The user key is entered (616) into a user interface that is in communication with generator (28), such that the calibrated settings are recalled (618) via the entry of the user key. The calibrated settings are transmitted (620) to the selected App, which is used (622) in a surgical procedure.

For the foregoing examples, it should be understood that the handle assemblies and/or end effectors may be reusable, autoclavable, and/or disposable. For instance, the foregoing end effectors may be disposable while the handle assemblies are reuseable and/or autoclavable. In addition, if internal power sources are used with the foregoing handle assemblies, the internal power sources may be rechargeable. For instance, the handle assemblies may be recharged using a plug in recharge, by removing and recharging the batteries, by induction, and/or by any other method as will be apparent to one of ordinary skill in the art in view of the teachings herein. Furthermore, alignment features or guides may be included to aid in the alignment and coupling of the end effectors with handle assemblies. Such guides may help prevent damage to the end effector and/or handle assembly during the assembly of the surgical instrument.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," issued Aug. 31, 2004, the disclosure of which is incorporated by reference herein.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for providing information from a generator in communication with a surgical instrument, the surgical instrument comprising a set of components, wherein the method comprises the steps of:
    (a) storing at least one unique identifier respectively associated with at least one of the set of components;
    (b) while using the surgical instrument during a medical procedure on a first patient, capturing a set of sensor data via a sensor disposed in at least one of the set of components;
    (c) capturing a set of generator data while the set of sensor data is captured;
    (d) creating a set of usage characteristics based upon the set of sensor data, the at least one unique identifier, and the set of generator data;
    (e) storing and associating the set of usage characteristics with a file; and
    (f) performing an analysis using the set of usage characteristics stored and associated with the file.

2. The method of claim 1, wherein the set of components comprises an end effector, wherein the set of usage characteristics comprises a time usage data of the end effector, the method further comprising:
    (a) calculating a cost based on the time usage data; and
    (b) displaying the cost via a display screen.

3. The method of claim 1, wherein the file comprises a patient file, the method further comprising analyzing the patient file to generate a report on usage of the surgical instrument.

4. The method of claim 1, further comprising displaying the analysis via a graphical user interface.

5. The method of claim 1, wherein:
    (i) the set of components comprises an end effector and a detachable transmission assembly,
    (ii) the at least one unique identifier respectively comprises a transmission identifier and an end effector identifier respectively associated with the detachable transmission assembly and the end effector,
    (iii) the set of sensor data separately describing the use of each of the detachable transmission assembly and the end effector during the medical procedure, and
    (iv) the set of usage characteristics comprises individual use data for each of the detachable transmission assembly and the end effector.

6. A method comprising:
    (a) associating at least one unique identifier respectively with at least one component of a surgical instrument, the surgical instrument comprising at least one sensor and a memory configured to store the at least one unique identifier;
    (b) communicatively coupling the surgical instrument to a server;
    (c) with the at least one sensor, capturing a set of usage characteristics that describe use of the surgical instrument during a medical procedure;
    (d) capturing a set of generator data while also capturing the set of usage characteristics;
    (e) transmitting the at least one unique identifier and the set of usage characteristics to the server;
    (f) storing and associating the set of usage characteristics and the set of generator data with the at least one unique identifier; and
    (g) performing an analysis of the medical procedure based on the set of usage characteristics, the set of generator data, and the at least one unique identifier.

7. The method of claim 6, the method further comprising:
    (a) associating the set of usage characteristics with a patient file based on the at least one unique identifier, wherein the patient file is associated with a patient on which the medical procedure was performed; and
    (b) calculating an overall cost of use for the surgical instrument for the medical procedure based upon the set of usage characteristics and the patient file;
    wherein the set of usage characteristics comprises at least two of the following:
        (i) duration of use,
        (ii) voltage conditions during use,
        (iii) total current used, or
        (iv) number of activations.

8. The method of claim 7, further comprising comparing the overall cost of use for the surgical instrument with a second overall cost of use for a second surgical instrument and displaying the results via a device communicatively connected with the server.

9. The method of claim 6, further comprising:
(a) communicatively coupling the surgical instrument to the server via a generator, wherein the generator is communicatively coupled to the server via a secure gateway;
(b) storing a secure key on the secure gateway; and
(c) when transmitting data to the server, requesting a remote secure key from the server and, where the secure key is validated by the remote secure key, transmitting the at least one unique identifier and the set of usage characteristics to the server.

10. The method of claim 6, further comprising configuring the server to:
(a) display a first graph view based on the set of usage characteristics in response to a request for the first graph view, wherein the first graph view shows steadiness of the surgical instrument and units of force applied to the surgical instrument during a period of time;
(b) display a second graph view based on the set of usage characteristics in response to a request for the second graph view, wherein the second graph view depicts power measured in watts generated by the surgical instrument and voltage measured in volts associated with the surgical instrument during a period of time;
(c) display a third graph view based on the set of usage characteristics in response to a request for the third graph view, wherein the third graph view depicts frequency slope measured in hertz per second and current measured in amps during a period of time; and
(d) display a fourth graph view based on the set of usage characteristics in response to a request for the fourth graph view, wherein the fourth graph view depicts frequency measured in hertz per second during a period of time.

11. The method of claim 6, further comprising:
(a) determining, from the set of usage characteristics, that a surgeon has used the surgical instrument in a potentially dangerous manner; and
(b) during a calibration process associated with the surgeon and a similar surgical instrument, adjusting a power provided by the generator to the similar surgical instrument in order to prevent unnecessary injury during a subsequent medical procedure performed by the surgeon.

12. The method of claim 11, wherein the potentially dangerous manner is applying an abnormally high amount of force to tissue while using the surgical instrument.

13. The method of claim 6, further comprising:
(a) associating the at least one unique identifier and the set of usage characteristics with a patient file, the patient file identifying a patient on which the medical procedure was performed; and
(b) displaying, via a device communicatively connected with the server, a plurality of surgical instrument components that are associated with the patient by unique identifiers.

14. The method of claim 6, further comprising capturing the set of usage characteristics comprising at least two of the following:
(i) steadiness of the surgical instrument over a period of time,
(ii) speed of a cutting portion of the surgical instrument over a period of time,
(iii) pressure on a cutting portion of the surgical instrument over a period of time,
(iv) power generated by the surgical instrument over a period of time,
(v) voltage conditions for the surgical instrument over a period of time,
(vi) tissue impedance for a tissue the surgical instrument is being applied to over a period of time,
(vii) current supplied to the surgical instrument over a period of time, or
(viii) frequency of a moving part of the surgical instrument over a period of time.

15. The method of claim 6, further comprising capturing the set of usage characteristics from at least two of the following:
(i) a piezoelectric accelerometer;
(ii) a gyroscope;
(iii) a pressure sensor;
(iv) a force transducer;
(v) an acoustic impedance sensor;
(vi) a thermal sensor; or
(vii) an electrical impedance sensor.

16. The method of claim 6, wherein the memory is configured to store unique identifiers corresponding to:
(i) a removable end effector,
(ii) a transmission assembly, and
(iii) a handle assembly.

17. The method of claim 6, further comprising:
(a) receiving a custom note that describes an aspect of the medical procedure;
(b) associating the custom note with the set of usage characteristics; and
(c) after performing the analysis, displaying the results of the analysis and the custom note,
wherein the custom note textually describes a condition that influenced the generation of the set of usage characteristics.

18. A surgical system comprising:
(a) a surgical instrument comprising a set of components;
(b) a generator usable to operate the surgical instrument, the generator comprising a memory, wherein the generator is coupled to the surgical instrument and the memory is configured to store at least one unique identifier respectively associated with at least one of the set of components;
(c) at least one sensor disposed within at least one of the set of components and the generator, wherein the at least one sensor is in communication with the generator; and
(d) a server comprising a processor;
wherein the processor is configured to:
(i) receive a set of usage characteristics and the at least one unique identifier, the set of usage characteristics comprising data produced by the at least one sensor during a medical procedure on a first patient,
(ii) store and associate the set of usage characteristics along with a set of generator data in a file,
(iii) perform an analysis using the set of usage characteristics and the set of generator data in the file, and
(iv) cause a set of results from the analysis to display on a receiving device.

19. The surgical system of claim 18, wherein the processor is further configured to, during the analysis, utilize the data produced by the at least one sensor to measure a surgeon performance.

20. The surgical system of claim 18 wherein the processor is further configured to, during the analysis, measure the cost effectiveness of the surgical instrument.

* * * * *